US005571718A

United States Patent [19]
Dunn et al.

[11] Patent Number: 5,571,718
[45] Date of Patent: Nov. 5, 1996

[54] CLONING AND EXPRESSION OF SOLUBLE TRUNCATED VARIANTS OF BORRELIA OSPA, OSPB AND VMP7

[75] Inventors: John J. Dunn, Bellport, N.Y.; Alan G. Barbour, San Antonio, Tex.

[73] Assignee: Associated Universities, Inc., Washington, D.C.

[21] Appl. No.: 941,523

[22] Filed: Sep. 8, 1992

Related U.S. Application Data

[63] Continuation-in-part of Ser. No. 632,072, Dec. 21, 1990, abandoned.

[51] Int. Cl.$^6$ .............................. C12N 1/20; C12N 15/70; C07K 13/00; C07H 21/04
[52] U.S. Cl. .................................. 435/252.3; 435/320.1; 530/359; 530/402; 536/23.7
[58] Field of Search .................................. 435/91.2, 69.1, 435/320.1, 252.3; 536/23.7, 24.33; 530/359, 402

[56] References Cited

FOREIGN PATENT DOCUMENTS

| 418827 | 9/1990 | European Pat. Off. . |
|---|---|---|
| 0465204A2 | 8/1992 | European Pat. Off. . |
| 9004411 | 3/1990 | WIPO . |
| 9200055 | 2/1992 | WIPO . |

OTHER PUBLICATIONS

Sam Brook et al. Molecular Cloning: A Laboratory Manual, 2nd ed. Cold Spring Harbor Laboratory Press, N.Y. (1989) pp. 8.46–8.49.

Wu, in Bacterial Outer Membranes as Model Systems, ed. Inouye John Wiley & Sons, New York, 1987, pp. 37–50.
Brandt et al., Infection & Immunity, vol. 58(4)*, pp. 983–1991 (Apr. 1990).
Howe et al. (8 Feb. 1985) Science, vol. 227, pp. 645–646.
Lin et al. (1980) Journal of Biol. Chem. vol. 255(3), pp. 1160–1163.
Kitten et al ., Proc. Natl. Acad. Sci., vol. 87, pp. 6077–6081, Aug. 1990.
Fikrig, et al., "Protection of Mice Against the Lyme Disease Agent by Immunizing with Recombinant OspA", Reports, Oct. 26, 1990.

*Primary Examiner*—W. Gary Jones
*Assistant Examiner*—Lisa Arthur
*Attorney, Agent, or Firm*—Margaret C. Bogosian

[57] ABSTRACT

A method is provided herein for preparing soluble recombinant variations of Borrelia lipoproteins such as *Borrelia burgdorferi* outer surface protein A (OspA) and outer surface protein B (OspB), and *B. hermsii* variable major protein 7 (Vmp7). The method includes synthesizing a set of oligonucleotide primers, amplifying the template DNA utilizing the PCR, purifying the amplification products, cloning the amplification products into a suitable expression vector, transforming a suitable host utilizing the cloned expression vector, cultivating the transformed host for protein production and subsequently isolating and purifying the resulting protein. Also provided are soluble, recombinant variations of *Borrelia burgdorferi* outer surface protein A (OspA), outer surface protein B (OspB), and *B. hermsii* variable major protein 7 (Vmp7). The expression vectors harboring DNA encoding the recombinant variations, pET9-OspA, pET9-OspB and pET9-Vmp7, as well as the *E. coli* host BL21(DE3)/pLysS transformed with each of these vectors, are also disclosed.

8 Claims, 23 Drawing Sheets

FIGURE 1

5' – CCGGGATCCA/TATGGC<u>TAAGCAAAATGTTAGC</u> – 3'

FIGURE 2

5' – GATATCTA/GATCT<u>TTATTTTAAAGCGTT</u> – 3'

FIGURE 3

5' – CCGGATCCA/T<u>ATGAAAAAATATTTATTGGGA</u> – 3'

FIGURE 4

1..........10..........20..........270......273
MetLysLysTyrLeuLeuGlyIleGlyIleIleAlaLeuLeuLeuAlaAlaCysLysLysGlnAsnValSerSerLeuAsp...GluIleLysAsnAlaLeuLys***
5'–AGAATATATTATGAAAAATATTTATTGGGAATAGGTCTAATATAGCCTTAATAGCATGTAAGCAAAATGTTAGCAGCCTTGAC...GAAATTAAAAACGCTTAAAATAAGGAGAA–3'
3'–TCTTATATAATACTTTTTATAAAATAACCCTTATCCAGATTATAAATCGGAATTATCGTACATTCGTTTTACAATCGTCGGAACAG...CTTTAATTTTTGCGAAATTTTATTCCTCTT–5'
150        170        190        210                                960    980

FIGURE 5

1..........10..........20..........270......273
MetLysLysTyrLeuLeuGlyIleGlyIleIleAlaLeuLeuLeuAlaAlaCysLysLysGlnAsnValSerSerLeuAsp...GluIleLysAsnAlaLeuLys***
5'–AGAATATATTATGAAAAATATTTATTGGGAATAGGTCTAATATTAGCCTTAATAGCATGTAAGCAAAATGTTAGCAGCCTTGAC...GAAATTAAAAACGCTTAAAATAAGGAGAA–3'
3'–TCTTATATAATACTTTTTATAAAATAACCCTTATCCAGATTATAATCGGAATTATCGTACATTCGTTTTACAATCGTCGGAACAG...CTTTAATTTTTGCGAAATTTTATTCCTCTT–5'
150        170        190        210                                960    980

```
                                                    (273)
              (18) ...........................................
         1   2   3 ..............................10 ...................258
         MetAlaLysGlnAsnValSerSerLeuAsp...GluIleLysAsnAlaLeuLys***

5'— CCGGGATCCATATGGCTAAGCAAAATGTTAGCAGCCTTGAC...GAAATTAAAAACGCTTAAAATAAAGATCTAGATATC — 3'
3'— GGCCCTAGGTATACCGATTCGTTTACAATCGTCGGAACAG...CTTTAATTTTTGCGAATTTTATTTCTAGATCTATAG — 5'
```

FIGURE 6

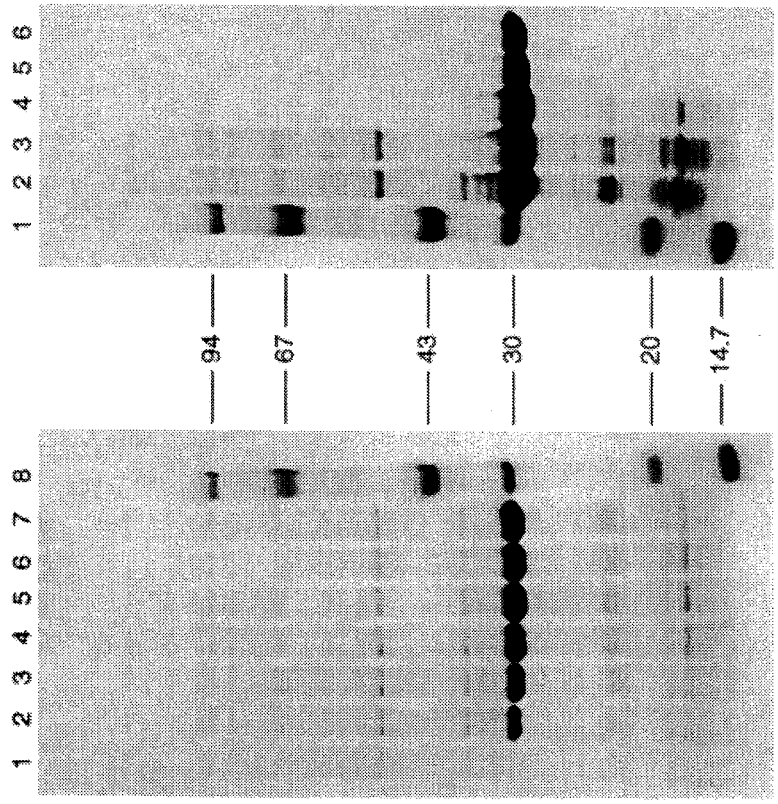
FIGURE 12
FIGURE 11
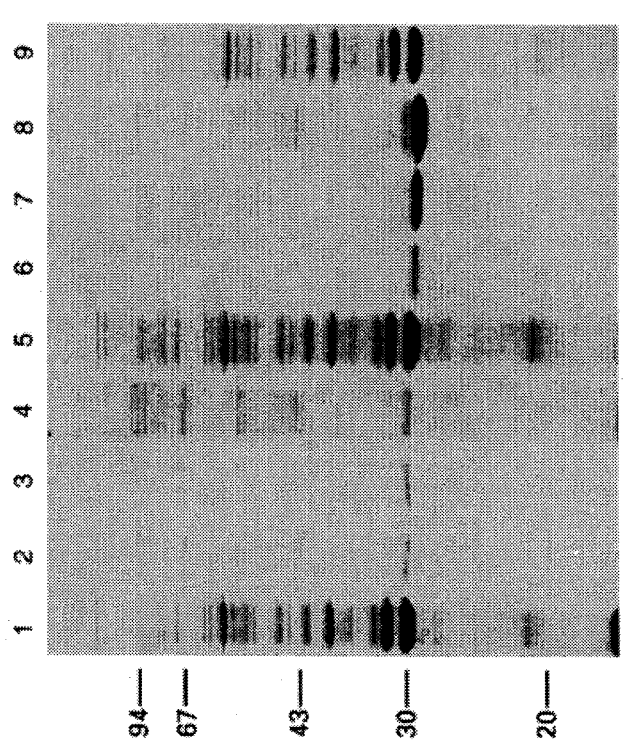
FIGURE 10

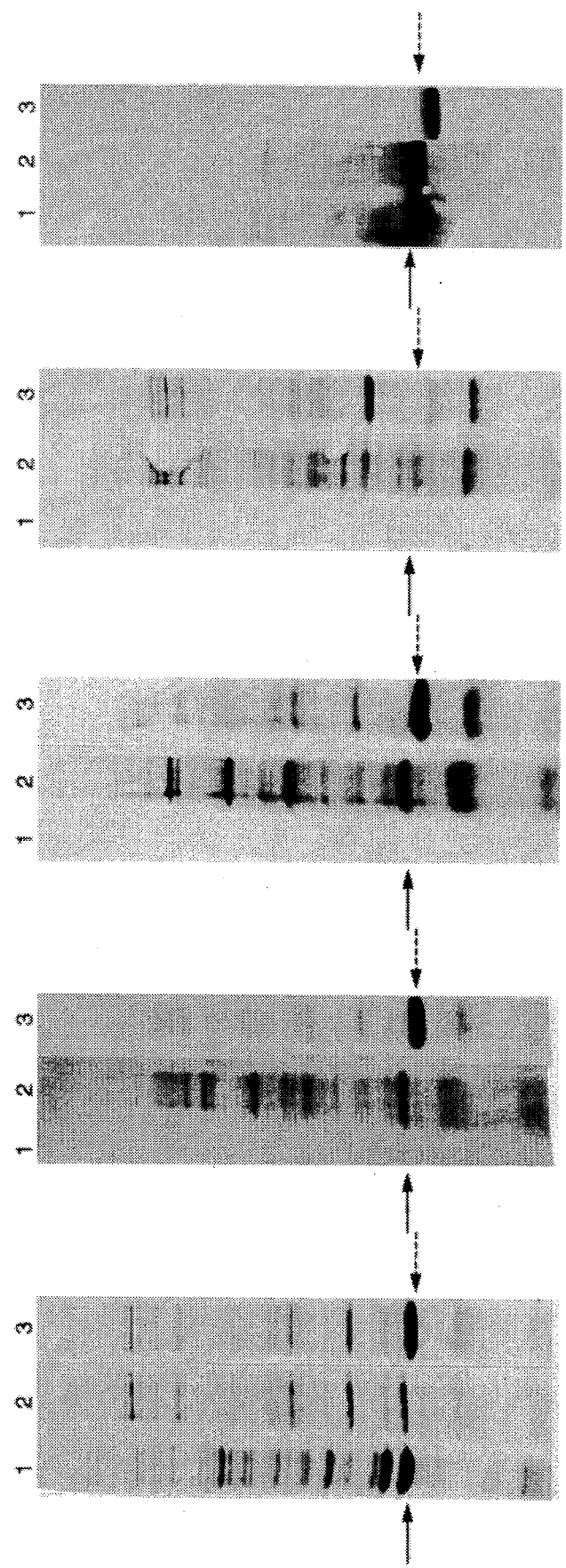

FIGURE 19a

1104    5' – CCGAGATCTCATATGAGATTATTAATAGGATTTGC – 3'    [ → DNA SYNTHESIS]

FIGURE 19b

1105    5' – CCGAGATCTCATATGGCACAAAAGGTGCTGAGTCAATTGG – 3'    [ → DNA SYNTHESIS]

FIGURE 19c

1106    5' – CCGATATCGGATCCTTATTTAAAGCGTTTTAAGC – 3'
         (3' – CGAATTTTGCGAAATTTATTCCTAGGCTATAGCC – 5')    [DNA SYNTHESIS ← ]

FIGURE 20a

Vmp7-2    5' – CCGAGATCTCATATGGCTGGACAACAACCAG – 3'    [ → DNA SYNTHESIS]

FIGURE 20b

Vmp7-3    5' – GATATCTAGATCTCACTTACTTGATTC – 3'

(3' – CTTAGTTCATTCACTCTAGATCTATAG – 5')    [DNA SYNTHESIS ← ]

FIGURE 21a

```
                                     10                          20
   1 ......................................................................... 290
     MetArgLeuLeuIleGlyPheAlaAlaLeuAlaLeuLeuIleGlyAlaGluLeuAlaLeuLeuIleGlyCysAlaGlnLysGlyAlaGluSerIleGly...GluLeuLysAsnAlaLeuLys***....296
5'- TAAGGAGAATTTATGAGATTATTAGGATTAGCGTTAGCTTAATAGGATGTGCACAAAAAGGTGCTGAGTCAATTGGT...GAGCTTAAAAACGCTTAAAATAATATAAG -3'
3'- ATTCCTCTAAATACTCTAATAATCCTAAACGAAATCGCAATGCGAAATTATCCTACACGTGTTTTCCACGACTCAGTTAACCA...CTCGAATTTTTGCGAAATTTTATTATATATTC -5'
         ↑                   ↑                                           ↑                                              ↑
        -10                 +1                                           60                                            891
```

FIGURE 21b

```
                                     10                          20
   1 ......................................................................... 290
     MetArgLeuLeuIleGlyPheAlaAlaLeuAlaLeuLeuIleGlyAlaGluLeuAlaLeuLeuIleGlyCysAlaGlnLysGlyAlaGluSerIleGly...GluLeuLysAsnAlaLeuLys***....296
5'- CCGAGATCTCATATGAGATTATTAGGATTGCTTAGCGTTAATAGGATGTGCACAAAAAGGTGCTGAGTCAATTGGT...GAGCTTAAAAACGCTTAAAATAAGGATCCGATATCGG -3'
3'- GGCTCTAGAGTATACTCTAATAATCCTAACGAATCGCAATTATCCTACACGTGTTTTCCACGACTCAGTTAACCA...CTCGAATTTTTGCGAAATTTATTCCTAGGCTATAGCC -5'
                                                                                                         ↑
                                                                                                        870
```

FIGURE 21c

```
                                                                        (296)
   (17) ............................................................................. 281
    1 2
    MetAlaGlnLysGlyAlaGluSerIleGly...GluLeuLysAsnAlaLeuLys***
5'- CCGAGATCTCATATGGCACAAAAAGGTGTTTTCCACGACTCAGTTAACCA...GAGCTTAAAAACGCTTAAAATAAGGATCCGATATCGG -3'
3'- GGCTCTAGAGTATACCGTGTTTTCCACGACTCAGTTAACCA...CTCGAATTTTTGCGAAATTTATTCCTAGGCTATAGCC -5'
```

FIGURE 22a

```
        1..........10..........Lys..........20..........30..........365.........369
        MetArgLysArgIleSerAlaIleIleSerIleIleIleMetThrValValLeuMetIleGlyCysGlyGlyGlnGlnProGlu...SerGluSerSerLys***
5' - GCACGTAAAAAAATGAGAAAAAGAATAAGTGCAATAATAAGTAAATATAAGTATAATTATATGACAGTGTTCTAATGATAAGGTTGTGTGGACAACAAGAA...TCAGAATCAAGTAAGTGAGAAGGCAGATTAA - 3'
3' - CGTGCATTTTTTTACTCTTTTTCTTATTCACGTTATTATTCATTTATATTCATATATTAATAATATCTGTCAACAAGATTACTATTCCAACACCTGTTGTTGGTCTT...AGTCTTAGTTCATTCACTCCGTCTAATT - 5'
         ↑         ↑                                    ↑          ↑                                                 ↑            ↑
        -10        +1                                   20         40                                                60          80                                                                1095        1110
```

FIGURE 22b

```
                                                                                                 (28)..................344
                                                                                                 1  .2  .3..............369
                                                                                                 MetAlaGlyGlnGlnProGlu...SerGluSerSerLys***
5' - CCGAGATCTCATATGGCTGGACAACAAGAA...TCAGAATCAAGTAAGTGAGATCTAGATATC - 3'
3' - GGCTCTAGAGTATACCGACCTGTTGTTCTT...AGTCTTAGTTCATTCACTCTAGATCTATAG - 5'
```

FIGURE 26

| | | | | | | | | | | | | | | | | |
|---|---|---|---|---|---|---|---|---|---|---|---|---|---|---|---|---|
| ATG | AAA | AAA | TAT | TTA | TTG | GGA | ATA | GGT | CTA | ATA | TTA | GCC | TTA | ATA | GCA | 48 |
| Met | Lys | Lys | Tyr | Leu | Leu | Gly | Ile | Gly | Leu | Ile | Leu | Ala | Leu | Ile | Ala | |
| | | | | 5 | | | | | 10 | | | | | 15 | | |
| TGT | AAG | CAA | AAT | GTT | AGC | AGC | CTT | GAC | GAG | AAA | AAC | AGC | GTT | TCA | GTA | 96 |
| Cys | Lys | Gln | Asn | Val | Ser | Ser | Leu | Asp | Glu | Lys | Asn | Ser | Val | Ser | Val | |
| | | | 20 | | | | | 25 | | | | | 30 | | | |
| GAT | TTG | CCT | GGT | GAA | ATG | AAA | GTT | CTT | GTA | AGC | AAA | GAA | AAA | AAC | AAA | 144 |
| Asp | Leu | Pro | Gly | Glu | Met | Lys | Val | Leu | Val | Ser | Lys | Glu | lys | Asn | Lys | |
| | | 35 | | | | | 40 | | | | | 45 | | | | |
| GAC | GGC | AAG | TAC | GAT | CTA | ATT | GCA | ACA | GTA | GAC | AAG | CTT | GAG | CTT | AAA | 192 |
| Asp | Gly | Lys | Tyr | Asp | Leu | Ile | Ala | Thr | Val | Asp | Lys | Leu | Glu | Leu | Lys | |
| | 50 | | | | | 55 | | | | | 60 | | | | | |
| GGA | ACT | TCT | GAT | AAA | AAC | AAT | GGA | TCT | GGA | GTA | CTT | GAA | GGC | GTA | AAA | 240 |
| Gly | Thr | Ser | Asp | Lys | Asn | Asn | Gly | Ser | Gly | Val | Leu | Glu | Gly | Val | Lys | |
| 65 | | | | | 70 | | | | | 75 | | | | | 80 | |
| GCT | GAC | AAA | AGT | AAA | GTA | AAA | TTA | ACA | ATT | TCT | GAC | GAT | CTA | GGT | CAA | 288 |
| Ala | Asp | Lys | Ser | Lys | Val | Lys | Leu | Thr | Ile | Ser | Asp | Asp | Leu | Gly | Gln | |
| | | | | 85 | | | | | 90 | | | | | 95 | | |
| ACC | ACA | CTT | GAA | GTT | TTC | AAA | GAA | GAT | GGC | AAA | ACA | CTA | GTA | TCA | AAA | 336 |
| Thr | Thr | Leu | Glu | Val | Phe | Lys | Glu | Asp | Gly | Lys | Thr | Leu | Val | Ser | Lys | |
| | | | 100 | | | | | 105 | | | | | 110 | | | |
| AAA | GTA | ACT | TCC | AAA | GAC | AAG | TCA | TCA | ACA | GAA | GAA | AAA | TTC | AAT | GAA | 384 |
| Lys | Val | Thr | Ser | Lys | Asp | Lys | Ser | Ser | Thr | Glu | Glu | Lys | Phe | Asn | Glu | |
| | | 115 | | | | | 120 | | | | | 125 | | | | |
| AAA | GGT | GAA | GTA | TCT | GAA | AAA | ATA | ATA | ACA | AGA | GCA | GAC | GGA | ACC | AGA | 432 |
| Lys | Gly | Glu | Val | Ser | Glu | Lys | Ile | Ile | Thr | Arg | Ala | Asp | Gly | Thr | Arg | |
| | 130 | | | | | 135 | | | | | 140 | | | | | |
| CTT | GAA | TAC | ACA | GGA | ATT | AAA | AGC | GAT | GGA | TCT | GGA | AAA | GCT | AAA | GAG | 480 |
| Leu | Glu | Tyr | Thr | Gly | Ile | Lys | Ser | Asp | Gly | Ser | Gly | Lys | Ala | Lys | Glu | |
| 145 | | | | | 150 | | | | | 155 | | | | | 160 | |
| GTT | TTA | AAA | GGC | TAT | GTT | CTT | GAA | GGA | ACT | CTA | ACT | GCT | GAA | AAA | ACA | 528 |
| Val | Leu | Lys | Gly | Tyr | Val | Leu | Glu | Gly | Thr | Leu | Thr | Ala | Glu | Lys | Thr | |
| | | | | 165 | | | | | 170 | | | | | 175 | | |
| ACA | TTG | GTG | GTT | AAA | GAA | GGA | ACT | GTT | ACT | TTA | AGC | AAA | AAT | ATT | TCA | 576 |
| Thr | Leu | Val | Val | Lys | Glu | Gly | Thr | Val | Thr | Leu | Ser | Lys | Asn | Ile | Ser | |
| | | | 180 | | | | | 185 | | | | | 190 | | | |
| AAA | TCT | GGG | GAA | GTT | TCA | GTT | GAA | CTT | AAT | GAC | ACT | GAC | AGT | AGT | GCT | 624 |
| Lys | Ser | Gly | Glu | Val | Ser | Val | Glu | Leu | Asn | Asp | Thr | Asp | Ser | Ser | Ala | |
| | | 195 | | | | | 200 | | | | | 205 | | | | |
| GCT | ACT | AAA | AAA | ACT | GCA | GCT | TGG | AAT | TCA | GGC | ACT | TCA | ACT | TTA | ACA | 672 |
| Ala | Thr | Lys | Lys | Thr | Ala | Ala | Trp | Asn | Ser | Gly | Thr | Ser | Thr | Leu | Thr | |
| | 210 | | | | | 215 | | | | | 220 | | | | | |
| ATT | ACT | GTA | AAC | AGT | AAA | AAA | ACT | AAA | GAC | CTT | GTG | TTT | ACA | AAA | GAA | 720 |
| Ile | Thr | Val | Asn | Ser | Lys | Lys | Thr | Lys | Asp | Leu | Val | Phe | Thr | Lys | Glu | |
| 225 | | | | | 230 | | | | | 235 | | | | | 240 | |
| AAC | ACA | ATT | ACA | GTA | CAA | CAA | TAC | GAC | TCA | AAT | GGC | ACC | AAA | TTA | GAG | 768 |
| Asn | Thr | Ile | Thr | Val | Gln | Gln | Tyr | Asp | Ser | Asn | Gly | Thr | Lys | Leu | Glu | |
| | | | | 245 | | | | | 250 | | | | | 255 | | |
| GGG | TCA | GCA | GTT | GAA | ATT | ACA | AAA | CTT | GAT | GAA | ATT | AAA | AAC | GCT | TTA | 816 |
| Gly | Ser | Ala | Val | Glu | Ile | Thr | Lys | Leu | Asp | Glu | Ile | Lys | Asn | Ala | Leu | |
| | | | 260 | | | | | 265 | | | | | 270 | | | |
| AAA | TAA | | | | | | | | | | | | | | | 822 |
| Lys | --- | | | | | | | | | | | | | | | |

FIGURE 27

| | | | | | | | | | | | | | | | | |
|---|---|---|---|---|---|---|---|---|---|---|---|---|---|---|---|---|
| ATG | GCT | AAG | CAA | AAT | GTT | AGC | AGC | CTT | GAC | GAG | AAA | AAC | AGC | GTT | TCA | 48 |
| Met | Ala | Lys | Gln | Asn | Val | Ser | Ser | Leu | Asp | Glu | Lys | Asn | Ser | Val | Ser | |
| | | | | 5 | | | | | 10 | | | | | 15 | | |
| GTA | GAT | TTG | CCT | GGT | GAA | ATG | AAA | GTT | CTT | GTA | AGC | AAA | GAA | AAA | AAC | 96 |
| Val | Asp | Leu | Pro | Gly | Glu | Met | Lys | Val | Leu | Val | Ser | Lys | Glu | Lys | Asn | |
| | | | 20 | | | | | 25 | | | | | 30 | | | |
| AAA | GAC | GGC | AAG | TAC | GAT | CTA | ATT | GCA | ACA | GTA | GAC | AAG | CTT | GAG | CTT | 144 |
| Lys | Asp | Gly | Lys | Tyr | Asp | Leu | Ile | Ala | Thr | Val | Asp | Lys | Leu | Glu | Leu | |
| | | 35 | | | | | 40 | | | | | 45 | | | | |
| AAA | GGA | ACT | TCT | GAT | AAA | AAC | AAT | GGA | TCT | GGA | GTA | CTT | GAA | GGC | GTA | 192 |
| Lys | Gly | Thr | Ser | Asp | Lys | Asn | Asn | Gly | Ser | Gly | Val | Leu | Glu | Gly | Val | |
| | 50 | | | | | 55 | | | | | 60 | | | | | |
| AAA | GCT | GAC | AAA | AGT | AAA | GTA | AAA | TTA | ACA | ATT | TCT | GAC | GAT | CTA | GGT | 240 |
| Lys | Ala | Asp | Lys | Ser | Lys | Val | Lys | Leu | Thr | Ile | Ser | Asp | Asp | Leu | Gly | |
| 65 | | | | 70 | | | | | 75 | | | | | | 80 | |
| CAA | ACC | ACA | CTT | GAA | GTT | TTC | AAA | GAA | GAT | GGC | AAA | ACA | CTA | GTA | TCA | 288 |
| Gln | Thr | Thr | Leu | Glu | Val | Phe | Lys | Glu | Asp | Gly | Lys | Thr | Leu | Val | Ser | |
| | | | | 85 | | | | | 90 | | | | | 95 | | |
| AAA | AAA | GTA | ACT | TCC | AAA | GAC | AAG | TCA | TCA | ACA | GAA | GAA | AAA | TTC | AAT | 336 |
| Lys | Lys | Val | Thr | Ser | Lys | Asp | Lys | Ser | Ser | Thr | Glu | Glu | Lys | Phe | Asn | |
| | | | 100 | | | | | 105 | | | | | 110 | | | |
| GAA | AAA | GGT | GAA | GTA | TCT | GAA | AAA | ATA | ATA | ACA | AGA | GCA | GAC | GGA | ACC | 384 |
| Glu | Lys | Gly | Glu | Val | Ser | Glu | Lys | Ile | Ile | Thr | Arg | Ala | Asp | Gly | Thr | |
| | | 115 | | | | | 120 | | | | | 125 | | | | |
| AGA | CTT | GAA | TAC | ACA | GGA | ATT | AAA | AGC | GAT | GGA | TCT | GGA | AAA | GCT | AAA | 432 |
| Arg | Leu | Glu | Tyr | Thr | Gly | Ile | Lys | Ser | Asp | Gly | Ser | Gly | Lys | Ala | Lys | |
| | 130 | | | | | 135 | | | | | 140 | | | | | |
| GAG | GTT | TTA | AAA | GGC | TAT | GTT | CTT | GAA | GGA | ACT | CTA | ACT | GCT | GAA | AAA | 480 |
| Glu | Val | Leu | Lys | Gly | Tyr | Val | Leu | Glu | Gly | Thr | Leu | Thr | Ala | Glu | Lys | |
| 145 | | | | | 150 | | | | | 155 | | | | | 160 | |
| ACA | ACA | TTG | GTG | GTT | AAA | GAA | GGA | ACT | GTT | ACT | TTA | AGC | AAA | AAT | ATT | 528 |
| Thr | Thr | Leu | Val | Val | Lys | Glu | Gly | Thr | Val | Thr | Leu | Ser | Lys | Asn | Ile | |
| | | | | 165 | | | | | 170 | | | | | 175 | | |
| TCA | AAA | TCT | GGG | GAA | GTT | TCA | GTT | GAA | CTT | AAT | GAC | ACT | GAC | AGT | AGT | 576 |
| Ser | Lys | Ser | Gly | Glu | Val | Ser | Val | Glu | Leu | Asn | Asp | Thr | Asp | Ser | Ser | |
| | | | 180 | | | | | 185 | | | | | 190 | | | |
| GCT | GCT | ACT | AAA | AAA | ACT | GCA | GCT | TGG | AAT | TCA | GGC | ACT | TCA | ACT | TTA | 624 |
| Ala | Ala | Thr | Lys | Lys | Thr | Ala | Ala | Trp | Asn | Ser | Gly | Thr | Ser | Thr | Leu | |
| | | 195 | | | | | 200 | | | | | 205 | | | | |
| ACA | ATT | ACT | GTA | AAC | AGT | AAA | AAA | ACT | AAA | GAC | CTT | GTG | TTT | ACA | AAA | 672 |
| Thr | Ile | Thr | Val | Asn | Ser | Lys | Lys | Thr | Lys | Asp | Leu | Val | Phe | Thr | Lys | |
| | 210 | | | | | 215 | | | | | 220 | | | | | |
| GAA | AAC | ACA | ATT | ACA | GTA | CAA | CAA | TAC | GAC | TCA | AAT | GGC | ACC | AAA | TTA | 720 |
| Glu | Asn | Thr | Ile | Thr | Val | Gln | Gln | Tyr | Asp | Ser | Asn | Gly | Thr | Lys | Leu | |
| 225 | | | | | 230 | | | | | 235 | | | | | 240 | |
| GAG | GGG | TCA | GCA | GTT | GAA | ATT | ACA | AAA | CTT | GAT | GAA | ATT | AAA | AAC | GCT | 768 |
| Glu | Gly | Ser | Ala | Val | Glu | Ile | Thr | Lys | Leu | Asp | Glu | Ile | Lys | Asn | Ala | |
| | | | | 245 | | | | | 250 | | | | | 255 | | |
| TTA | AAA | TAA | | | | | | | | | | | | | | 777 |
| Leu | Lys | --- | | | | | | | | | | | | | | |

FIGURE 28

```
ATG GCA CAA AAA GGT GCT GAG TCA ATT GGT TCT CAA AAA GAA AAT GAT    48
Met Ala Gln Lys Gly Ala Glu Ser Ile Gly Ser Gln Lys Glu Asn Asp
              5                   10                  15
CTA AAC CTT GAA GAC TCT AGT AAA AAA TCA CAT CAA AAC GCT AAA CAA    96
Leu Asn Leu Glu Asp Ser Ser Lys Lys Ser His Gln Asn Ala Lys Gln
              20                  25                  30
GAC CTT CCT GCG GTG ACA GAA GAC TCA GTG TCT TTG TTT AAT GGT AAT   144
Asp Leu Pro Ala Val Thr Glu Asp Ser Val Ser Leu Phe Asn Gly Asn
              35                  40                  45
AAA ATT TTT GTA AGC AAA GAA AAA AAT AGC TCC GGC AAA TAT GAT TTA   192
Lys Ile Phe Val Ser Lys Glu Lys Asn Ser Ser Gly Lys Tyr Asp Leu
              50                  55                  60
AGA GCA ACA ATT GAT CAG GTT GAA CTT AAA GGA ACT TCC GAT AAA AAC   240
Arg Ala Thr Ile Asp Gln Val Glu Leu Lys Gly Thr Ser Asp Lys Asn
65                  70                  75                  80
AAT GGT TCT GGA ACC CTT GAA GGT TCA AAG CCT GAC AAG AGT AAA GTA   288
Asn Gly Ser Gly Thr Leu Glu Gly Ser Lys Pro Asp Lys Ser Lys Val
              85                  90                  95
AAA TTA ACA GTT TCT GCT GAT TTA AAC ACA GTA ACC TTA GAA GCA TTT   336
Lys Leu Thr Val Ser Ala Asp Leu Asn Thr Val Thr Leu Glu Ala Phe
              100                 105                 110
GAT GCC AGC AAC CAA AAA ATT TCA AGT AAA GTT ACT AAA AAA CAG GGG   384
Asp Ala Ser Asn Gln Lys Ile Ser Ser Lys Val Thr Lys Lys Gln Gly
              115                 120                 125
TCA ATA ACA GAG GAA ACT CTC AAA GCT AAT AAA TTA GAC TCA AAG AAA   432
Ser Ile Thr Glu Glu Thr Leu Lys Ala Asn Lys Leu Asp Ser Lys Lys
    130                 135                 140
TTA ACA AGA TCA AAC GGA ACT ACA CTT GAA TAC TCA CAA ATA ACA GAT   480
Leu Thr Arg Ser Asn Gly Thr Thr Leu Glu Tyr Ser Gln Ile Thr Asp
145                 150                 155                 160
GCT GAC AAT GCT ACA AAA GCA GTA GAA ACT CTA AAA AAT AGC ATT AAG   528
Ala Asp Asn Ala Thr Lys Ala Val Glu Thr Leu Lys Asn Ser Ile Lys
              165                 170                 175
CTT GAA GGA AGT CTT GTA GTC GGA AAA ACA ACA GTG GAA ATT AAA GAA   576
Leu Glu Gly Ser Leu Val Val Gly Lys Thr Thr Val Glu Ile Lys Glu
              180                 185                 190
GGT ACT GTT ACT CTA AAA AGA GAA ATT GAA AAA GAT GGA AAA GTA AAA   624
Gly Thr Val Thr Leu Lys Arg Glu Ile Glu Lys Asp Gly Lys Val Lys
              195                 200                 205
GTC TTT TTG AAT GAC ACT GCA GGT TCT AAC AAA AAA ACA GGT AAA TGG   672
Val Phe Leu Asn Asp Thr Ala Gly Ser Asn Lys Lys Thr Gly Lys Trp
              210                 215                 220
GAA GAC AGT ACT AGC ACT TTA ACA ATT AGT GCT GAC AGC AAA AAA ACT   720
Glu Asp Ser Thr Ser Thr Leu Thr Ile Ser Ala Asp Ser Lys Lys Thr
225                 230                 235                 240
AAA GAT TTG GTG TTC TTA ACA GAT GGT ACA ATT ACA GTA CAA CAA TAC   768
Lys Asp Leu Val Phe Leu Thr Asp Gly Thr Ile Thr Val Gln Gln Tyr
              245                 250                 255
AAC ACA GCT GGA ACC AGC CTA GAA GGA TCA GCA AGT GAA ATT AAA AAT   816
Asn Thr Ala Gly Thr Ser Leu Glu Gly Ser Ala Ser Glu Ile Lys Asn
              260                 265                 270
CTT TCA GAG CTT AAA AAC GCT TTA AAA TAA                           846
Leu Ser Glu Leu Lys Asn Ala Leu Lys ---
              275                 280
```

FIGURE 29a

| | | | | | | | | | | | | | | | | |
|---|---|---|---|---|---|---|---|---|---|---|---|---|---|---|---|---|
| ATG | GCT | GGA | CAA | CAA | CCA | GAA | GCA | GGT | AAG | ACC | GGA | GTA | TCA | GGA | GGA | 48 |
| Met | Ala | Gly | Gln | Gln | Pro | Glu | Ala | Gly | Lys | Thr | Gly | Val | Ser | Gly | Gly | |
| | | | | 5 | | | | | 10 | | | | | 15 | | |
| GTA | AAT | GGA | AAT | TTA | GGC | AAT | TCA | CTA | ATG | GAA | TTA | GGT | AGG | AGT | GCG | 96 |
| Val | Asn | Gly | Asn | Leu | Gly | Asn | Ser | Leu | Met | Glu | Leu | Gly | Arg | Ser | Ala | |
| | | | | 20 | | | | 25 | | | | | 30 | | | |
| GAG | AAT | GCT | TTT | TAC | GCA | TTT | ATA | GAG | TTA | GTG | TCA | GAT | GTG | TTG | GGA | 144 |
| Glu | Asn | Ala | Phe | Tyr | Ala | Phe | Ile | Glu | Leu | Val | Ser | Asp | Val | Leu | Gly | |
| | | 35 | | | | | 40 | | | | | 45 | | | | |
| TTT | ACT | GCA | AAA | TCA | GAT | ACA | ACT | AAG | CAA | GAA | GTA | GGA | GGT | TAT | TTT | 192 |
| Phe | Thr | Ala | Lys | Ser | Asp | Thr | Thr | Lys | Gln | Glu | Val | Gly | Gly | Tyr | Phe | |
| | | 50 | | | | | 55 | | | | | 60 | | | | |
| AAC | AGC | CTA | GGT | GCG | AAG | CTT | GGA | GAG | GCG | TCA | AAT | GAC | TTG | GAA | CAA | 240 |
| Asn | Ser | Leu | Gly | Ala | Lys | Leu | Gly | Glu | Ala | Ser | Asn | Asp | Leu | Glu | Gln | |
| 65 | | | | | 70 | | | | | 75 | | | | | 80 | |
| GTA | GCA | GTA | AAA | GCA | GAA | ACA | GGT | GTT | GAT | AAA | AGC | GAT | TCA | TCA | AAA | 288 |
| Val | Ala | Val | Lys | Ala | Glu | Thr | Gly | Val | Asp | Lys | Ser | Asp | Ser | Ser | Lys | |
| | | | | 85 | | | | | 90 | | | | | 95 | | |
| AAT | CCA | ATT | AGA | GAA | GCG | GTT | AAT | GAA | GCT | AAG | GAA | GTT | TTA | GGT | ACA | 336 |
| Asn | Pro | Ile | Arg | Glu | Ala | Val | Asn | Glu | Ala | Lys | Glu | Val | Leu | Gly | Thr | |
| | | | 100 | | | | | 105 | | | | | 110 | | | |
| TAA | AAA | GGA | TAT | GTA | GAA | TCT | TTA | GGA | ACA | ATA | GGC | GAT | TCT | AAT | CCA | 384 |
| Leu | Lys | Gly | Tyr | Val | Glu | Ser | Leu | Gly | Thr | Ile | Gly | Asp | Ser | Asn | Pro | |
| | | 115 | | | | | 120 | | | | | 125 | | | | |
| GTA | GGT | TAT | GCA | AAT | AAT | GCT | GCT | GGT | TCA | GGA | ACA | ACA | GCA | GCT | GAT | 432 |
| Val | Gly | Tyr | Ala | Asn | Asn | Ala | Ala | Gly | Ser | Gly | Thr | Thr | Ala | Ala | Asp | |
| | 130 | | | | | 135 | | | | | 140 | | | | | |
| GAT | GAA | TTA | AGG | AAA | GCT | TTT | AAA | GCA | TTG | CAA | GAA | ATA | GTC | AAA | GCA | 480 |
| Asp | Glu | Leu | Arg | Lys | Ala | Phe | Lys | Ala | Leu | Gln | Glu | Ile | Val | Lys | Ala | |
| 145 | | | | | 150 | | | | | 155 | | | | | 160 | |
| GCA | ACA | GAT | GCA | GGT | GTT | AAA | GCA | TTA | AAA | ATA | GGA | GCT | ACT | ACA | CTA | 528 |
| Ala | Thr | Asp | Ala | Gly | Val | Lys | Ala | Leu | Lys | Ile | Gly | Ala | Thr | Thr | Leu | |
| | | | | 165 | | | | | 170 | | | | | 175 | | |
| CAA | GCA | AAT | GGA | GGA | GCA | GAT | AAT | AAA | GAG | GGT | GCT | AAG | ATA | TTA | GCT | 576 |
| Gln | Ala | Asn | Gly | Gly | Ala | Asp | Asn | Lys | Glu | Gly | Ala | Lys | Ile | Leu | Ala | |
| | | | 180 | | | | | 185 | | | | | 190 | | | |
| ACA | AGT | GGT | GGT | AAT | CCA | GCA | GCA | GCA | GAT | GTA | GCT | AAA | GCA | GCA | GCA | 624 |
| Thr | Ser | Gly | Gly | Asn | Pro | Ala | Ala | Ala | Asp | Val | Ala | Lys | Ala | Ala | Ala | |
| | | 195 | | | | | 200 | | | | | 205 | | | | |

FIGURE 29b

| | | | | | | | | | | | | | | | | |
|---|---|---|---|---|---|---|---|---|---|---|---|---|---|---|---|---|
| ATA | CTA | TCA | AGC | GTA | AGT | GGT | GAA | GAG | ATG | TTA | AGC | TCA | ATA | GTT | AAA | 672 |
| Ile | Leu | Ser | Ser | Val | Ser | Gly | Glu | Glu | Met | Leu | Ser | Ser | Ile | Val | Lys | |
| | | 210 | | | | 215 | | | | | 220 | | | | | |
| TCA | GGA | GAG | AAT | GAT | GCG | CAG | CTA | GCA | GCA | GCT | GCA | GAT | GGA | AAT | ACA | 720 |
| Ser | Gly | Glu | Asn | Asp | Ala | Gln | Leu | Ala | Ala | Ala | Ala | Asp | Gly | Asn | Thr | |
| 225 | | | | | 230 | | | | | 235 | | | | | 240 | |
| AGT | GCA | ATT | TCT | TTT | GCA | AAA | GGA | GGT | TCA | GAT | GCT | CAC | TTA | GCA | GGT | 768 |
| Ser | Ala | Ile | Ser | Phe | Ala | Lys | Gly | Gly | Ser | Asp | Ala | His | Leu | Ala | Gly | |
| | | | | 245 | | | | | 250 | | | | | 255 | | |
| GCA | AAT | ACT | CCA | AAA | GCA | GCA | GCA | GTA | GCA | GGA | GGA | ATA | GCA | TTA | CGT | 816 |
| Ala | Asn | Thr | Pro | Lys | Ala | Ala | Ala | Val | Ala | Gly | Gly | Ile | Ala | Leu | Arg | |
| | | | 260 | | | | | 265 | | | | | 270 | | | |
| TCA | TTA | GTG | AAG | ACA | GGT | AAA | TTA | GCA | GCA | GGA | GCA | GCA | GAT | AAT | GCT | 864 |
| Ser | Leu | Val | Lys | Thr | Gly | Lys | Leu | Ala | Ala | Gly | Ala | Ala | Asp | Asn | Ala | |
| | | 275 | | | | | 280 | | | | | 285 | | | | |
| ACA | GGA | GGG | GGG | AAA | GAA | GTA | CAA | GGA | GTA | GGA | GTG | GCT | GCA | GCA | AAT | 912 |
| Thr | Gly | Gly | Gly | Lys | Glu | Val | Gln | Gly | Val | Gly | Val | Ala | Ala | Ala | Asn | |
| | 290 | | | | | 295 | | | | | 300 | | | | | |
| AAG | CTG | TTA | AGA | GCG | GTA | GAA | GAT | GTA | ATT | AAG | AAG | ACA | GTA | AAG | AAT | 960 |
| Lys | Leu | Leu | Arg | Ala | Val | Glu | Asp | Val | Ile | Lys | Lys | Thr | Val | Lys | Asn | |
| 305 | | | | | 310 | | | | | 315 | | | | | 320 | |
| GTT | CTT | GAG | AAA | GCA | AAA | GAA | AAA | ATA | GAT | AAA | GCA | AGA | GGT | TCA | CAA | 1008 |
| Val | Leu | Glu | Lys | Ala | Lys | Glu | Lys | Ile | Asp | Lys | Ala | Arg | Gly | Ser | Gln | |
| | | | | 325 | | | | | 330 | | | | | 335 | | |
| GAG | CCA | GTT | TCA | GAA | TCA | AGT | AAG | TGA | | | | | | | | 1035 |
| Glu | Pro | Val | Ser | Glu | Ser | Ser | Lys | --- | | | | | | | | |
| | | | 340 | | | | | | | | | | | | | |

5,571,718

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 822 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

| ATGAAAAAAT | ATTTATTGGG | AATAGGTCTA | ATATTAGCCT | TAATAGCATG | TAAGCAAAAT | 60 |
| GTTAGCAGCC | TTGACGAGAA | AAACAGCGTT | TCAGTAGATT | TGCCTGGTGA | AATGAAAGTT | 120 |
| CTTGTAAGCA | AAGAAAAAAA | CAAAGACGGC | AAGTACGATC | TAATTGCAAC | AGTAGACAAG | 180 |
| CTTGAGCTTA | AAGGAACTTC | TGATAAAAAC | AATGGATCTG | GAGTACTTGA | AGGCGTAAAA | 240 |
| GCTGACAAAA | GTAAAGTAAA | ATTAACAATT | TCTGACGATC | TAGGTCAAAC | CACACTTGAA | 300 |
| GTTTTCAAAG | AAGATGGCAA | AACACTAGTA | TCAAAAAAAG | TAACTTCCAA | AGACAAGTCA | 360 |
| TCAACAGAAG | AAAAATTCAA | TGAAAAGGT  | GAAGTATCTG | AAAAAATAAT | AACAAGAGCA | 420 |
| GACGGAACCA | GACTTGAATA | CACAGGAATT | AAAAGCGATG | GATCTGGAAA | AGCTAAAGAG | 480 |
| GTTTTAAAAG | GCTATGTTCT | TGAAGGAACT | CTAACTGCTG | AAAAAACAAC | ATTGGTGGTT | 540 |
| AAAGAAGGAA | CTGTTACTTT | AAGCAAAAAT | ATTTCAAAAT | CTGGGGAAGT | TTCAGTTGAA | 600 |
| CTTAATGACA | CTGACAGTAG | TGCTGCTACT | AAAAAAACTG | CAGCTTGGAA | TTCAGGCACT | 660 |
| TCAACTTTAA | CAATTACTGT | AAACAGTAAA | AAAACTAAAG | ACCTTGTGTT | TACAAAAGAA | 720 |
| AACACAATTA | CAGTACAACA | ATACGACTCA | AATGGCACCA | AATTAGAGGG | GTCAGCAGTT | 780 |
| GAAATTACAA | AACTTGATGA | AATTAAAAAC | GCTTTAAAAT | AA         |            | 822 |

( 2 ) INFORMATION FOR SEQ ID NO:2:

( i ) SEQUENCE CHARACTERISTICS:
        ( A ) LENGTH: 273 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Lys Lys Tyr Leu Leu Gly Ile Gly Leu Ile Leu Ala Leu Ile Ala
  1               5                  10                  15

Cys Lys Gln Asn Val Ser Ser Leu Asp Glu Lys Asn Ser Val Ser Val
             20                  25                  30

Asp Leu Pro Gly Glu Met Lys Val Leu Val Ser Lys Glu Lys Asn Lys
         35                  40                  45

Asp Gly Lys Tyr Asp Leu Ile Ala Thr Val Asp Lys Leu Glu Leu Lys
     50                  55                  60

Gly Thr Ser Asp Lys Asn Asn Gly Ser Gly Val Leu Glu Gly Val Lys
 65                  70                  75                  80

Ala Asp Lys Ser Lys Val Lys Leu Thr Ile Ser Asp Asp Leu Gly Gln
             85                  90                  95

Thr Thr Leu Glu Val Phe Lys Glu Asp Gly Lys Thr Leu Val Ser Lys
        100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
                180                 185                 190
```

|       |       | Lys   | Ser   | Gly   | Glu   | Val   | Ser   | Val   | Glu   | Leu   | Asn   | Asp   | Thr   | Asp   | Ser   | Ser   | Ala   |
|---|---|---|---|---|---|---|---|---|---|---|---|---|---|---|---|---|---|
|       |       |       |       | 195   |       |       |       |       | 200   |       |       |       | 205   |       |       |       |       |
|       |       | Ala   | Thr   | Lys   | Lys   | Thr   | Ala   | Ala   | Trp   | Asn   | Ser   | Gly   | Thr   | Ser   | Thr   | Leu   | Thr   |
|       |       |       | 210   |       |       |       |       | 215   |       |       |       |       | 220   |       |       |       |       |
|       |       | Ile   | Thr   | Val   | Asn   | Ser   | Lys   | Lys   | Thr   | Lys   | Asp   | Leu   | Val   | Phe   | Thr   | Lys   | Glu   |
|       |       | 225   |       |       |       |       | 230   |       |       |       |       | 235   |       |       |       |       | 240   |
|       |       | Asn   | Thr   | Ile   | Thr   | Val   | Gln   | Gln   | Tyr   | Asp   | Ser   | Asn   | Gly   | Thr   | Lys   | Leu   | Glu   |
|       |       |       |       |       |       | 245   |       |       |       |       | 250   |       |       |       |       | 255   |       |
|       |       | Gly   | Ser   | Ala   | Val   | Glu   | Ile   | Thr   | Lys   | Leu   | Asp   | Glu   | Ile   | Lys   | Asn   | Ala   | Leu   |
|       |       |       |       |       | 260   |       |       |       |       | 265   |       |       |       |       | 270   |       |       |
|       |       | Lys   |       |       |       |       |       |       |       |       |       |       |       |       |       |       |       |

( 2 ) INFORMATION FOR SEQ ID NO:3:

( i ) SEQUENCE CHARACTERISTICS:
    ( A ) LENGTH: 777 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:3:

| ATGGCTAAGC | AAAATGTTAG | CAGCCTTGAC | GAGAAAAACA | GCGTTTCAGT | AGATTTGCCT | 60 |
|---|---|---|---|---|---|---|
| GGTGAAATGA | AAGTTCTTGT | AAGCAAAGAA | AAAACAAAG  | ACGGCAAGTA | CGATCTAATT | 120 |
| GCAACAGTAG | ACAAGCTTGA | GCTTAAAGGA | ACTTCTGATA | AAACAATGG  | ATCTGGAGTA | 180 |
| CTTGAAGGCG | TAAAAGCTGA | CAAAAGTAAA | GTAAATTAA  | CAATTTCTGA | CGATCTAGGT | 240 |
| CAAACCACAC | TTGAAGTTTT | CAAAGAAGAT | GGCAAAACAC | TAGTATCAAA | AAAAGTAACT | 300 |
| TCCAAAGACA | AGTCATCAAC | AGAAGAAAAA | TTCAATGAAA | AAGGTGAAGT | ATCTGAAAAA | 360 |
| ATAATAACAA | GAGCAGACGG | AACCAGACTT | GAATACACAG | GAATTAAAAG | CGATGGATCT | 420 |
| GGAAAAGCTA | AAGAGGTTTT | AAAAGGCTAT | GTTCTTGAAG | AACTCTAAC  | TGCTGAAAAA | 480 |
| ACAACATTGG | TGGTTAAAGA | AGGAACTGTT | ACTTTAAGCA | AAAATATTTC | AAAATCTGGG | 540 |
| GAAGTTTCAG | TTGAACTTAA | TGACACTGAC | AGTAGTGCTG | CTACTAAAAA | AACTGCAGCT | 600 |
| TGGAATTCAG | GCACTTCAAC | TTTAACAATT | ACTGTAAACA | GTAAAAAAAC | TAAAGACCTT | 660 |
| GTGTTTACAA | AAGAAAACAC | AATTACAGTA | CAACAATACG | ACTCAAATGG | CACCAAATTA | 720 |
| GAGGGGTCAG | CAGTTGAAAT | TACAAAACTT | GATGAAATTA | AAAACGCTTT | AAAATAA    | 777 |

( 2 ) INFORMATION FOR SEQ ID NO:4:

( i ) SEQUENCE CHARACTERISTICS:
    ( A ) LENGTH: 258 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:4:

|       |       | Met   | Ala   | Lys   | Gln   | Asn   | Val   | Ser   | Ser   | Leu   | Asp   | Glu   | Lys   | Asn   | Ser   | Val   | Ser   |
|---|---|---|---|---|---|---|---|---|---|---|---|---|---|---|---|---|---|
|       |       | 1     |       |       |       | 5     |       |       |       |       | 10    |       |       |       |       | 15    |       |
|       |       | Val   | Asp   | Leu   | Pro   | Gly   | Glu   | Met   | Lys   | Val   | Leu   | Val   | Ser   | Lys   | Glu   | Lys   | Asn   |
|       |       |       |       |       | 20    |       |       |       |       | 25    |       |       |       |       | 30    |       |       |
|       |       | Lys   | Asp   | Gly   | Lys   | Tyr   | Asp   | Leu   | Ile   | Ala   | Thr   | Val   | Asp   | Lys   | Leu   | Glu   | Leu   |
|       |       |       |       | 35    |       |       |       |       | 40    |       |       |       |       | 45    |       |       |       |
|       |       | Lys   | Gly   | Thr   | Ser   | Asp   | Lys   | Asn   | Asn   | Gly   | Ser   | Gly   | Val   | Leu   | Glu   | Gly   | Val   |

|  | 50 |  |  |  | 55 |  |  |  | 60 |  |  |  |  |
|---|---|---|---|---|---|---|---|---|---|---|---|---|---|
| Lys 65 | Ala | Asp | Lys | Ser 70 | Val | Lys | Leu | Thr | Ile 75 | Ser | Asp | Asp | Leu | Gly 80 |
| Gln | Thr | Thr | Leu | Glu 85 | Val | Phe | Lys | Glu | Asp 90 | Gly | Lys | Thr | Leu | Val 95 | Ser |
| Lys | Lys | Val | Thr 100 | Ser | Lys | Asp | Lys | Ser 105 | Ser | Thr | Glu | Glu | Lys 110 | Phe | Asn |
| Glu | Lys | Gly 115 | Glu | Val | Ser | Glu | Lys 120 | Ile | Ile | Thr | Arg | Ala 125 | Asp | Gly | Thr |
| Arg | Leu 130 | Glu | Tyr | Thr | Gly | Ile 135 | Lys | Ser | Asp | Gly | Ser 140 | Gly | Lys | Ala | Lys |
| Glu 145 | Val | Leu | Lys | Gly | Tyr 150 | Val | Leu | Glu | Gly | Thr 155 | Leu | Thr | Ala | Glu | Lys 160 |
| Thr | Thr | Leu | Val | Val 165 | Lys | Glu | Gly | Thr | Val 170 | Thr | Leu | Ser | Lys | Asn 175 | Ile |
| Ser | Lys | Ser | Gly 180 | Glu | Val | Ser | Val | Glu 185 | Leu | Asn | Asp | Thr | Asp 190 | Ser | Ser |
| Ala | Ala | Thr 195 | Lys | Lys | Thr | Ala | Ala 200 | Trp | Asn | Ser | Gly | Thr 205 | Ser | Thr | Leu |
| Thr | Ile 210 | Thr | Val | Asn | Ser | Lys 215 | Lys | Thr | Lys | Asp | Leu 220 | Val | Phe | Thr | Lys |
| Glu 225 | Asn | Thr | Ile | Thr | Val 230 | Gln | Gln | Tyr | Asp | Ser 235 | Asn | Gly | Thr | Lys | Leu 240 |
| Glu | Gly | Ser | Ala | Val 245 | Glu | Ile | Thr | Lys | Leu 250 | Asp | Glu | Ile | Lys | Asn 255 | Ala |
| Leu | Lys |

( 2 ) INFORMATION FOR SEQ ID NO:5:

( i ) SEQUENCE CHARACTERISTICS:
( A ) LENGTH: 774 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:5:

```
GCTAAGCAAA ATGTTAGCAG CCTTGACGAG AAAAACAGCG TTTCAGTAGA TTTGCCTGGT      60
GAAATGAAAG TTCTTGTAAG CAAAGAAAAA AACAAGACG GCAAGTACGA TCTAATTGCA      120
ACAGTAGACA AGCTTGAGCT TAAAGGAACT TCTGATAAAA ACAATGGATC TGGAGTACTT      180
GAAGGCGTAA AAGCTGACAA AAGTAAAGTA AAATTAACAA TTTCTGACGA TCTAGGTCAA      240
ACCACACTTG AAGTTTTCAA AGAAGATGGC AAAACACTAG TATCAAAAAA AGTAACTTCC      300
AAAGACAAGT CATCAACAGA AGAAAAATTC AATGAAAAAG GTGAAGTATC TGAAAAAATA      360
ATAACAAGAG CAGACGGAAC CAGACTTGAA TACACAGGAA TTAAAGCGA TGGATCTGGA      420
AAAGCTAAAG AGGTTTTAAA AGGCTATGTT CTTGAAGGAA CTCTAACTGC TGAAAAAACA      480
ACATTGGTGG TTAAAGAAGG AACTGTTACT TTAAGCAAAA ATATTTCAAA ATCTGGGGAA      540
GTTTCAGTTG AACTTAATGA CACTGACAGT AGTGCTGCTA CTAAAAAAAC TGCAGCTTGG      600
AATTCAGGCA CTTCAACTTT AACAATTACT GTAAACAGTA AAAAAACTAA AGACCTTGTG      660
TTTACAAAAG AAAACACAAT TACAGTACAA CAATACGACT CAAATGGCAC CAAATTAGAG      720
GGGTCAGCAG TTGAAATTAC AAAACTTGAT GAAATTAAAA ACGCTTTAAA ATAA          774
```

( 2 ) INFORMATION FOR SEQ ID NO:6:

( i ) SEQUENCE CHARACTERISTICS:
        ( A ) LENGTH: 257 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Ala Lys Gln Asn Val Ser Ser Leu Asp Glu Lys Asn Ser Val Ser Val
 1               5                  10                  15

Asp Leu Pro Gly Glu Met Lys Val Leu Val Ser Lys Glu Lys Asn Lys
            20                  25                  30

Asp Gly Lys Tyr Asp Leu Ile Ala Thr Val Asp Lys Leu Glu Leu Lys
        35                  40                  45

Gly Thr Ser Asp Lys Asn Asn Gly Ser Gly Val Leu Glu Gly Val Lys
    50                  55                  60

Ala Asp Lys Ser Lys Val Lys Leu Thr Ile Ser Asp Asp Leu Gly Gln
65                  70                  75                  80

Thr Thr Leu Glu Val Phe Lys Glu Asp Gly Lys Thr Leu Val Ser Lys
                85                  90                  95

Lys Val Thr Ser Lys Asp Lys Ser Ser Thr Glu Glu Lys Phe Asn Glu
            100                 105                 110

Lys Gly Glu Val Ser Glu Lys Ile Ile Thr Arg Ala Asp Gly Thr Arg
        115                 120                 125

Leu Glu Tyr Thr Gly Ile Lys Ser Asp Gly Ser Gly Lys Ala Lys Glu
    130                 135                 140

Val Leu Lys Gly Tyr Val Leu Glu Gly Thr Leu Thr Ala Glu Lys Thr
145                 150                 155                 160

Thr Leu Val Val Lys Glu Gly Thr Val Thr Leu Ser Lys Asn Ile Ser
                165                 170                 175

Lys Ser Gly Glu Val Ser Val Glu Leu Asn Asp Thr Asp Ser Ser Ala
            180                 185                 190

Ala Thr Lys Lys Thr Ala Ala Trp Asn Ser Gly Thr Ser Thr Leu Thr
        195                 200                 205

Ile Thr Val Asn Ser Lys Lys Thr Lys Asp Leu Val Phe Thr Lys Glu
    210                 215                 220

Asn Thr Ile Thr Val Gln Gln Tyr Asp Ser Asn Gly Thr Lys Leu Glu
225                 230                 235                 240

Gly Ser Ala Val Glu Ile Thr Lys Leu Asp Glu Ile Lys Asn Ala Leu
                245                 250                 255

Lys
```

( 2 ) INFORMATION FOR SEQ ID NO:7:

( i ) SEQUENCE CHARACTERISTICS:
        ( A ) LENGTH: 774 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

```
ATGAAGCAAA ATGTTAGCAG CCTTGACGAG AAAAACAGCG TTTCAGTAGA TTTGCCTGGT     60

GAAATGAAAG TTCTTGTAAG CAAAGAAAAA AACAAAGACG GCAAGTACGA TCTAATTGCA    120

ACAGTAGACA AGCTTGAGCT TAAAGGAACT TCTGATAAAA ACAATGGATC TGGAGTACTT    180
```

| GAAGGCGTAA | AAGCTGACAA | AAGTAAAGTA | AAATTAACAA | TTTCTGACGA | TCTAGGTCAA | 240 |
| ACCACACTTG | AAGTTTTCAA | AGAAGATGGC | AAAACACTAG | TATCAAAAAA | AGTAACTTCC | 300 |
| AAAGACAAGT | CATCAACAGA | AGAAAAATTC | AATGAAAAAG | GTGAAGTATC | TGAAAAAATA | 360 |
| ATAACAAGAG | CAGACGGAAC | CAGACTTGAA | TACACAGGAA | TTAAAAGCGA | TGGATCTGGA | 420 |
| AAAGCTAAAG | AGGTTTTAAA | AGGCTATGTT | CTTGAAGGAA | CTCTAACTGC | TGAAAAAACA | 480 |
| ACATTGGTGG | TTAAAGAAGG | AACTGTTACT | TTAAGCAAAA | ATATTTCAAA | ATCTGGGGAA | 540 |
| GTTTCAGTTG | AACTTAATGA | CACTGACAGT | AGTGCTGCTA | CTAAAAAAAC | TGCAGCTTGG | 600 |
| AATTCAGGCA | CTTCAACTTT | AACAATTACT | GTAAACAGTA | AAAAAACTAA | AGACCTTGTG | 660 |
| TTTACAAAAG | AAAACACAAT | TACAGTACAA | CAATACGACT | CAAATGGCAC | CAAATTAGAG | 720 |
| GGGTCAGCAG | TTGAAATTAC | AAAACTTGAT | GAAATTAAAA | ACGCTTTAAA | ATAA | 774 |

( 2 ) INFORMATION FOR SEQ ID NO:8:

( i ) SEQUENCE CHARACTERISTICS:
 ( A ) LENGTH: 257 amino acids
 ( B ) TYPE: amino acid
 ( C ) STRANDEDNESS: single
 ( D ) TOPOLOGY: linear ( i i ) MOLECULE TYPE: protein ( x i ) SEQUENCE DESCRIPTION: SEQ ID NO:8:

```
Met Lys Gln Asn Val Ser Ser Leu Asp Glu Lys Asn Ser Val Ser Val
 1               5                  10                  15

Asp Leu Pro Gly Glu Met Lys Val Leu Ser Lys Glu Lys Asn Lys
             20              25                  30

Asp Gly Lys Tyr Asp Leu Ile Ala Thr Val Asp Lys Leu Glu Leu Lys
         35                  40                  45

Gly Thr Ser Asp Lys Asn Asn Gly Ser Gly Val Leu Glu Gly Val Lys
     50                  55                  60

Ala Asp Lys Ser Lys Val Lys Leu Thr Ile Ser Asp Asp Leu Gly Gln
65                  70                  75                  80

Thr Thr Leu Glu Val Phe Lys Glu Asp Gly Lys Thr Leu Val Ser Lys
                 85                  90                  95

Lys Val Thr Ser Lys Asp Lys Ser Ser Thr Glu Glu Lys Phe Asn Glu
                100                 105                 110

Lys Gly Glu Val Ser Glu Lys Ile Ile Thr Arg Ala Asp Gly Thr Arg
            115                 120                 125

Leu Glu Tyr Thr Gly Ile Lys Ser Asp Gly Ser Gly Lys Ala Lys Glu
    130                 135                 140

Val Leu Lys Gly Tyr Val Leu Glu Gly Thr Leu Thr Ala Glu Lys Thr
145                 150                 155                 160

Thr Leu Val Val Lys Glu Gly Thr Val Thr Leu Ser Lys Asn Ile Ser
                165                 170                 175

Lys Ser Gly Glu Val Ser Val Glu Leu Asn Asp Thr Asp Ser Ser Ala
            180                 185                 190

Ala Thr Lys Lys Thr Ala Ala Trp Asn Ser Gly Thr Ser Thr Leu Thr
        195                 200                 205

Ile Thr Val Asn Ser Lys Lys Thr Lys Asp Leu Val Phe Thr Lys Glu
    210                 215                 220

Asn Thr Ile Thr Val Gln Gln Tyr Asp Ser Asn Gly Thr Lys Leu Glu
225                 230                 235                 240

Gly Ser Ala Val Glu Ile Thr Lys Leu Asp Glu Ile Lys Asn Ala Leu
```

|     | 245 |     | 250 |     | 255 |     |

Lys (2) INFORMATION FOR SEQ ID NO:9:

(i) SEQUENCE CHARACTERISTICS:
      (A) LENGTH: 771 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:9:

| | | | | | | |
|---|---|---|---|---|---|---|
| AAGCAAAATG | TTAGCAGCCT | TGACGAGAAA | AACAGCGTTT | CAGTAGATTT | GCCTGGTGAA | 60 |
| ATGAAAGTTC | TTGTAAGCAA | AGAAAAAAAC | AAAGACGGCA | AGTACGATCT | AATTGCAACA | 120 |
| GTAGACAAGC | TTGAGCTTAA | AGGAACTTCT | GATAAAAACA | ATGGATCTGG | AGTACTTGAA | 180 |
| GGCGTAAAAG | CTGACAAAAG | TAAAGTAAAA | TTAACAATTT | CTGACGATCT | AGGTCAAACC | 240 |
| ACACTTGAAG | TTTTCAAAGA | AGATGGCAAA | ACACTAGTAT | CAAAAAAAGT | AACTTCCAAA | 300 |
| GACAAGTCAT | CAACAGAAGA | AAAATTCAAT | GAAAAGGTG | AAGTATCTGA | AAAAATAATA | 360 |
| ACAAGAGCAG | ACGGAACCAG | ACTTGAATAC | ACAGGAATTA | AAAGCGATGG | ATCTGGAAAA | 420 |
| GCTAAAGAGG | TTTTAAAAGG | CTATGTTCTT | GAAGGAACTC | TAACTGCTGA | AAAAACAACA | 480 |
| TTGGTGGTTA | AAGAAGGAAC | TGTTACTTTA | AGCAAAAATA | TTTCAAAATC | TGGGGAAGTT | 540 |
| TCAGTTGAAC | TTAATGACAC | TGACAGTAGT | GCTGCTACTA | AAAAAACTGC | AGCTTGGAAT | 600 |
| TCAGGCACTT | CAACTTTAAC | AATTACTGTA | AACAGTAAAA | AAACTAAAGA | CCTTGTGTTT | 660 |
| ACAAAGAAA | ACACAATTAC | AGTACAACAA | TACGACTCAA | ATGGCACCAA | ATTAGAGGGG | 720 |
| TCAGCAGTTG | AAATTACAAA | ACTTGATGAA | ATTAAAAACG | CTTTAAAATA | A | 771 |

(2) INFORMATION FOR SEQ ID NO:10:

(i) SEQUENCE CHARACTERISTICS:
      (A) LENGTH: 256 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:10:

| Lys | Gln | Asn | Val | Ser | Ser | Leu | Asp | Glu | Lys | Asn | Ser | Val | Ser | Val | Asp |
|---|---|---|---|---|---|---|---|---|---|---|---|---|---|---|---|
| 1 | | | | 5 | | | | | 10 | | | | | 15 | |
| Leu | Pro | Gly | Glu | Met | Lys | Val | Leu | Val | Ser | Lys | Glu | Lys | Asn | Lys | Asp |
| | | | 20 | | | | | 25 | | | | | 30 | | |
| Gly | Lys | Tyr | Asp | Leu | Ile | Ala | Thr | Val | Asp | Lys | Leu | Glu | Leu | Lys | Gly |
| | | 35 | | | | | 40 | | | | | 45 | | | |
| Thr | Ser | Asp | Lys | Asn | Asn | Gly | Ser | Gly | Val | Leu | Glu | Gly | Val | Lys | Ala |
| | 50 | | | | | 55 | | | | | 60 | | | | |
| Asp | Lys | Ser | Lys | Val | Lys | Leu | Thr | Ile | Ser | Asp | Asp | Leu | Gly | Gln | Thr |
| 65 | | | | | 70 | | | | | 75 | | | | | 80 |
| Thr | Leu | Glu | Val | Phe | Lys | Glu | Asp | Gly | Lys | Thr | Leu | Val | Ser | Lys | Lys |
| | | | | 85 | | | | | 90 | | | | | 95 | |
| Val | Thr | Ser | Lys | Asp | Lys | Ser | Ser | Thr | Glu | Glu | Lys | Phe | Asn | Glu | Lys |
| | | | 100 | | | | | 105 | | | | | 110 | | |
| Gly | Glu | Val | Ser | Glu | Lys | Ile | Ile | Thr | Arg | Ala | Asp | Gly | Thr | Arg | Leu |
| | | 115 | | | | | 120 | | | | | 125 | | | |

| | | | | | | | | | | | | | | |
|---|---|---|---|---|---|---|---|---|---|---|---|---|---|---|
|Glu|Tyr|Thr|Gly|Ile|Lys|Ser|Asp|Gly|Ser|Gly|Lys|Ala|Lys|Glu|Val|
| |130| | | |135| | | |140| | | | | |
|Leu|Lys|Gly|Tyr|Val|Leu|Glu|Gly|Thr|Leu|Thr|Ala|Glu|Lys|Thr|Thr|
|145| | | |150| | | |155| | | | | |160|
|Leu|Val|Val|Lys|Glu|Gly|Thr|Val|Thr|Leu|Ser|Lys|Asn|Ile|Ser|Lys|
| | | |165| | | |170| | | |175| | | |
|Ser|Gly|Glu|Val|Ser|Val|Glu|Leu|Asn|Asp|Thr|Asp|Ser|Ser|Ala|Ala|
| | |180| | | |185| | | |190| | | | |
|Thr|Lys|Lys|Thr|Ala|Ala|Trp|Asn|Ser|Gly|Thr|Ser|Thr|Leu|Thr|Ile|
| |195| | | |200| | | |205| | | | | |
|Thr|Val|Asn|Ser|Lys|Lys|Thr|Lys|Asp|Leu|Val|Phe|Thr|Lys|Glu|Asn|
|210| | | |215| | | |220| | | | | | |
|Thr|Ile|Thr|Val|Gln|Gln|Tyr|Asp|Ser|Asn|Gly|Thr|Lys|Leu|Glu|Gly|
|225| | | |230| | | |235| | | | | |240|
|Ser|Ala|Val|Glu|Ile|Thr|Lys|Leu|Asp|Glu|Ile|Lys|Asn|Ala|Leu|Lys|
| | | |245| | | |250| | | |255| | | |

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CCGGGATCCA TATGGCTAAG CAAAATGTTA GC                            32

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GATATCTAGA TCTTTATTTT AAAGCGTT                              28

( 2 ) INFORMATION FOR SEQ ID NO:13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CCGGATCCAT ATGAAAAAAT ATTTATTGGG A                            31

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:14:

CCGAGATCTC ATATGAGATT ATTAATAGGA TTTGC    35

(2) INFORMATION FOR SEQ ID NO:15:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:15:

CCGAGATCTC ATATGGCACA AAAAGGTGCT GAGTCAATTG G    41

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:16:

CCGATATCGG ATCCTTATTT TAAAGCGTTT TTAAGC    36

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

CCGAGATCTC ATATGGCTGG ACAACAACCA G    31

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:18:

GATATCTAGA TCTCACTTAC TTGATTC    27

(2) INFORMATION FOR SEQ ID NO:19:

(i) SEQUENCE CHARACTERISTICS:
        (A) LENGTH: 891 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:19:

ATGAGATTAT TAATAGGATT TGCTTTAGCG TTAGCTTTAA TAGGATGTGC ACAAAAGGT    60

GCTGAGTCAA TTGGTTCTCA AAAAGAAAAT GATCTAAACC TTGAAGACTC TAGTAAAAAA    120

```
TCACATCAAA  ACGCTAAACA  AGACCTTCCT  GCGGTGACAG  AAGACTCAGT  GTCTTTGTTT    180

AATGGTAATA  AAATTTTGT   AAGCAAAGAA  AAAAATAGCT  CCGGCAAATA  TGATTTAAGA    240

GCAACAATTG  ATCAGGTTGA  ACTTAAGGA   ACTTCCGATA  AAACAATGG   TTCTGGAACC    300

CTTGAAGGTT  CAAAGCCTGA  CAAGAGTAAA  GTAAATTAA   CAGTTTCTGC  TGATTTAAAC    360

ACAGTAACCT  TAGAAGCATT  TGATGCCAGC  AACCAAAAAA  TTTCAAGTAA  AGTTACTAAA    420

AAACAGGGGT  CAATAACAGA  GGAAACTCTC  AAAGCTAATA  AATTAGACTC  AAAGAAATTA    480

ACAAGATCAA  ACGGAACTAC  ACTTGAATAC  TCACAAATAA  CAGATGCTGA  CAATGCTACA    540

AAAGCAGTAG  AAACTCTAAA  AAATAGCATT  AAGCTTGAAG  GAAGTCTTGT  AGTCGGAAAA    600

ACAACAGTGG  AAATTAAAGA  AGGTACTGTT  ACTCTAAAAA  GAGAAATTGA  AAAAGATGGA    660

AAAGTAAAAG  TCTTTTTGAA  TGACACTGCA  GGTTCTAACA  AAAAACAGG   TAAATGGGAA    720

GACAGTACTA  GCACTTTAAC  AATTAGTGCT  GACAGCAAAA  AAACTAAAGA  TTTGGTGTTC    780

TTAACAGATG  GTACAATTAC  AGTACAACAA  TACAACACAG  CTGGAACCAG  CCTAGAAGGA    840

TCAGCAAGTG  AAATTAAAAA  TCTTTCAGAG  CTTAAAAACG  CTTTAAAATA  A             891
```

( 2 ) INFORMATION FOR SEQ ID NO:20:

( i ) SEQUENCE CHARACTERISTICS:
        ( A ) LENGTH: 1110 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

```
ATGAGAAAAA  GAATAAGTGC  AATAATTAAT  AAGTTAAATA  TAAGTATAAT  TATTATGACA     60

GTTGTTCTAA  TGATAGGTTG  TGGACAACAA  CCAGAAGCAG  GTAAGACCGG  AGTATCAGGA    120

GGAGTAAATG  GAAATTTAGG  CAATTCACTA  ATGGAATTAG  GTAGGAGTGC  GGAGAATGCT    180

TTTTACGCAT  TTATAGAGTT  AGTGTCAGAT  GTGTTGGGAT  TTACTGCAAA  ATCAGATACA    240

ACTAAGCAAG  AAGTAGGAGG  TTATTTTAAC  AGCCTAGGTG  CGAAGCTTGG  AGAGGCGTCA    300

AATGACTTGG  AACAAGTAGC  AGTAAAAGCA  GAAACAGGTG  TTGATAAAAG  CGATTCATCA    360

AAAAATCCAA  TTAGAGAAGC  GGTTAATGAA  GCTAAGGAAG  TTTTAGGTAC  ATTAAAAGGA    420

TATGTAGAAT  CTTTAGGAAC  AATAGGCGAT  TCTAATCCAG  TAGGTTATGC  AAATAATGCT    480

GCTGGTTCAG  GAACAACAGC  AGCTGATGAT  GAATTAAGGA  AAGCTTTTAA  AGCATTGCAA    540

GAAATAGTCA  AAGCAGCAAC  AGATGCAGGT  GTTAAAGCAT  TAAAAATAGG  AGCTACTACA    600

CTACAAGCAA  ATGGAGGAGC  AGATAATAAA  GAGGGTGCTA  AGATATTAGC  TACAAGTGGT    660

GGTAATCCAG  CAGCAGCAGA  TGTAGCTAAA  GCAGCAGCAA  TACTATCAAG  CGTAAGTGGT    720

GAAGAGATGT  TAAGCTCAAT  AGTTAAATCA  GGAGAGAATG  ATGCGCAGCT  AGCAGCAGCT    780

GCAGATGGAA  ATACAAGTGC  AATTTCTTTT  GCAAAAGGAG  GTTCAGATGC  TCACTTAGCA    840

GGTGCAAATA  CTCCAAAAGC  AGCAGCAGTA  GCAGGAGGAA  TAGCATTACG  TTCATTAGTG    900

AAGACAGGTA  AATTAGCAGC  AGGAGCAGCA  GATAATGCTA  CAGGAGGGGG  GAAAGAAGTA    960

CAAGGAGTAG  GAGTGGCTGC  AGCAAATAAG  CTGTTAAGAG  CGGTAGAAGA  TGTAATTAAG   1020

AAGACAGTAA  AGAATGTTCT  TGAGAAAGCA  AAAGAAAAAA  TAGATAAAGC  AAGAGGTTCA   1080

CAAGAGCCAG  TTTCAGAATC  AAGTAAGTGA                                       1110
```

( 2 ) INFORMATION FOR SEQ ID NO:21:

( i ) SEQUENCE CHARACTERISTICS:
 ( A ) LENGTH: 846 base pairs
 ( B ) TYPE: nucleic acid
 ( C ) STRANDEDNESS: double
 ( D ) TOPOLOGY: linear ( i i ) MOLECULE TYPE: DNA (genomic)

( x i ) SEQUENCE DESCRIPTION: SEQ ID NO:21:

| | | | | | | |
|---|---|---|---|---|---|---|
| ATGGCACAAA | AAGGTGCTGA | GTCAATTGGT | TCTCAAAAAG | AAAATGATCT | AAACCTTGAA | 60 |
| GACTCTAGTA | AAAAATCACA | TCAAACGCT | AAACAAGACC | TTCCTGCGGT | GACAGAAGAC | 120 |
| TCAGTGTCTT | TGTTTAATGG | TAATAAAATT | TTTGTAAGCA | AAGAAAAAAA | TAGCTCCGGC | 180 |
| AAATATGATT | TAAGAGCAAC | AATTGATCAG | GTTGAACTTA | AAGGAACTTC | CGATAAAAAC | 240 |
| AATGGTTCTG | GAACCCTTGA | AGGTTCAAAG | CCTGACAAGA | GTAAAGTAAA | ATTAACAGTT | 300 |
| TCTGCTGATT | TAAACACAGT | AACCTTAGAA | GCATTTGATG | CCAGCAACCA | AAAAATTTCA | 360 |
| AGTAAAGTTA | CTAAAAAACA | GGGGTCAATA | ACAGAGGAAA | CTCTCAAAGC | TAATAAATTA | 420 |
| GACTCAAAGA | AATTAACAAG | ATCAAACGGA | ACTACACTTG | AATACTCACA | AATAACAGAT | 480 |
| GCTGACAATG | CTACAAAAGC | AGTAGAAACT | CTAAAAAATA | GCATTAAGCT | TGAAGGAAGT | 540 |
| CTTGTAGTCG | GAAAACAAC | AGTGGAAATT | AAAGAAGGTA | CTGTTACTCT | AAAAAGAGAA | 600 |
| ATTGAAAAAG | ATGGAAAAGT | AAAAGTCTTT | TTGAATGACA | CTGCAGGTTC | TAACAAAAAA | 660 |
| ACAGGTAAAT | GGGAAGACAG | TACTAGCACT | TTAACAATTA | GTGCTGACAG | CAAAAAAACT | 720 |
| AAAGATTTGG | TGTTCTTAAC | AGATGGTACA | ATTACAGTAC | AACAATACAA | CACAGCTGGA | 780 |
| ACCAGCCTAG | AAGGATCAGC | AAGTGAAATT | AAAAATCTTT | CAGAGCTTAA | AAACGCTTTA | 840 |
| AAATAA | | | | | | 846 |

( 2 ) INFORMATION FOR SEQ ID NO:22:

( i ) SEQUENCE CHARACTERISTICS:
 ( A ) LENGTH: 1035 base pairs
 ( B ) TYPE: nucleic acid
 ( C ) STRANDEDNESS: double
 ( D ) TOPOLOGY: linear ( i i ) MOLECULE TYPE: DNA (genomic)

( x i ) SEQUENCE DESCRIPTION: SEQ ID NO:22:

| | | | | | | |
|---|---|---|---|---|---|---|
| ATGGCTGGAC | AACAACCAGA | AGCAGGTAAG | ACCGGAGTAT | CAGGAGGAGT | AAATGGAAAT | 60 |
| TTAGGCAATT | CACTAATGGA | ATTAGGTAGG | AGTGCGGAGA | ATGCTTTTTA | CGCATTTATA | 120 |
| GAGTTAGTGT | CAGATGTGTT | GGGATTTACT | GCAAAATCAG | ATACAACTAA | GCAAGAAGTA | 180 |
| GGAGGTTATT | TTAACAGCCT | AGGTGCGAAG | CTTGGAGAGG | CGTCAAATGA | CTTGGAACAA | 240 |
| GTAGCAGTAA | AAGCAGAAAC | AGGTGTTGAT | AAAAGCGATT | CATCAAAAAA | TCCAATTAGA | 300 |
| GAAGCGGTTA | ATGAAGCTAA | GGAAGTTTTA | GGTACATTAA | AAGGATATGT | AGAATCTTTA | 360 |
| GGAACAATAG | GCGATTCTAA | TCCAGTAGGT | TATGCAAATA | ATGCTGCTGG | TTCAGGAACA | 420 |
| ACAGCAGCTG | ATGATGAATT | AAGGAAAGCT | TTTAAAGCAT | TGCAAGAAAT | AGTCAAAGCA | 480 |
| GCAACAGATG | CAGGTGTTAA | AGCATTAAAA | ATAGGAGCTA | CTACACTACA | AGCAAATGGA | 540 |
| GGAGCAGATA | ATAAAGAGGG | TGCTAAGATA | TTAGCTACAA | GTGGTGGTAA | TCCAGCAGCA | 600 |
| GCAGATGTAG | CTAAAGCAGC | AGCAATACTA | TCAAGCGTAA | GTGGTGAAGA | GATGTTAAGC | 660 |
| TCAATAGTTA | AATCAGGAGA | GAATGATGCG | CAGCTAGCAG | CAGCTGCAGA | TGGAAATACA | 720 |
| AGTGCAATTT | CTTTTGCAAA | AGGAGGTTCA | GATGCTCACT | TAGCAGGTGC | AAATACTCCA | 780 |

```
AAAGCAGCAG  CAGTAGCAGG  AGGAATAGCA  TTACGTTCAT  TAGTGAAGAC  AGGTAAATTA       840

GCAGCAGGAG  CAGCAGATAA  TGCTACAGGA  GGGGGGAAAG  AAGTACAAGG  AGTAGGAGTG       900

GCTGCAGCAA  ATAAGCTGTT  AAGAGCGGTA  GAAGATGTAA  TTAAGAAGAC  AGTAAAGAAT       960

GTTCTTGAGA  AAGCAAAAGA  AAAAATAGAT  AAAGCAAGAG  GTTCACAAGA  GCCAGTTTCA      1020

GAATCAAGTA  AGTGA                                                           1035
```

( 2 ) INFORMATION FOR SEQ ID NO:23:

( i ) SEQUENCE CHARACTERISTICS:
        ( A ) LENGTH: 281 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

```
Met Ala Gln Lys Gly Ala Glu Ser Ile Gly Ser Gln Lys Glu Asn Asp
 1               5                  10                  15

Leu Asn Leu Glu Asp Ser Ser Lys Lys Ser His Gln Asn Ala Lys Gln
            20                  25                  30

Asp Leu Pro Ala Val Thr Glu Asp Ser Val Ser Leu Phe Asn Gly Asn
        35                  40                  45

Lys Ile Phe Val Ser Lys Glu Lys Asn Ser Ser Gly Lys Tyr Asp Leu
    50                  55                  60

Arg Ala Thr Ile Asp Gln Val Glu Leu Lys Gly Thr Ser Asp Lys Asn
65                  70                  75                  80

Asn Gly Ser Gly Thr Leu Glu Gly Ser Lys Pro Asp Lys Ser Lys Val
                85                  90                  95

Lys Leu Thr Val Ser Ala Asp Leu Asn Thr Val Thr Leu Glu Ala Phe
           100                 105                 110

Asp Ala Ser Asn Gln Lys Ile Ser Ser Lys Val Thr Lys Lys Gln Gly
       115                 120                 125

Ser Ile Thr Glu Glu Thr Leu Lys Ala Asn Lys Leu Asp Ser Lys Lys
   130                 135                 140

Leu Thr Arg Ser Asn Gly Thr Thr Leu Glu Tyr Ser Gln Ile Thr Asp
145                 150                 155                 160

Ala Asp Asn Ala Thr Lys Ala Val Glu Thr Leu Lys Asn Ser Ile Lys
                165                 170                 175

Leu Glu Gly Ser Leu Val Val Gly Lys Thr Thr Val Glu Ile Lys Glu
            180                 185                 190

Gly Thr Val Thr Leu Lys Arg Glu Ile Glu Lys Asp Gly Lys Val Lys
        195                 200                 205

Val Phe Leu Asn Asp Thr Ala Gly Ser Asn Lys Lys Thr Gly Lys Trp
    210                 215                 220

Glu Asp Ser Thr Ser Thr Leu Thr Ile Ser Ala Asp Ser Lys Lys Thr
225                 230                 235                 240

Lys Asp Leu Val Phe Leu Thr Asp Gly Thr Ile Thr Val Gln Gln Tyr
                245                 250                 255

Asn Thr Ala Gly Thr Ser Leu Glu Gly Ser Ala Ser Glu Ile Lys Asn
            260                 265                 270

Leu Ser Glu Leu Lys Asn Ala Leu Lys
           275                 280
```

( 2 ) INFORMATION FOR SEQ ID NO:24:

(i) SEQUENCE CHARACTERISTICS:
   (A) LENGTH: 344 amino acids
   (B) TYPE: amino acid
   (C) STRANDEDNESS: single
   (D) TOPOLOGY: linear (ii) MOLECULE TYPE: protein (xi) SEQUENCE DESCRIPTION: SEQ ID NO:24:

```
Met Ala Gly Gln Gln Pro Glu Ala Gly Lys Thr Gly Val Ser Gly Gly
1               5                  10                 15

Val Asn Gly Asn Leu Gly Asn Ser Leu Met Glu Leu Gly Arg Ser Ala
            20                 25                 30

Glu Asn Ala Phe Tyr Ala Phe Ile Glu Leu Val Ser Asp Val Leu Gly
        35                 40                 45

Phe Thr Ala Lys Ser Asp Thr Thr Lys Gln Glu Val Gly Gly Tyr Phe
    50                 55                 60

Asn Ser Leu Gly Ala Lys Leu Gly Glu Ala Ser Asn Asp Leu Glu Gln
65                  70                 75                 80

Val Ala Val Lys Ala Glu Thr Gly Val Asp Lys Ser Asp Ser Ser Lys
                85                 90                 95

Asn Pro Ile Arg Glu Ala Val Asn Glu Ala Lys Glu Val Leu Gly Thr
            100                105                110

Leu Lys Gly Tyr Val Glu Ser Leu Gly Thr Ile Gly Asp Ser Asn Pro
        115                120                125

Val Gly Tyr Ala Asn Asn Ala Ala Gly Ser Gly Thr Thr Ala Ala Asp
    130                135                140

Asp Glu Leu Arg Lys Ala Phe Lys Ala Leu Gln Glu Ile Val Lys Ala
145                150                155                160

Ala Thr Asp Ala Gly Val Lys Ala Leu Lys Ile Gly Ala Thr Thr Leu
                165                170                175

Gln Ala Asn Gly Gly Ala Asp Asn Lys Glu Gly Ala Lys Ile Leu Ala
            180                185                190

Thr Ser Gly Gly Asn Pro Ala Ala Ala Asp Val Ala Lys Ala Ala Ala
        195                200                205

Ile Leu Ser Ser Val Ser Gly Glu Glu Met Leu Ser Ser Ile Val Lys
    210                215                220

Ser Gly Glu Asn Asp Ala Gln Leu Ala Ala Ala Ala Asp Gly Asn Thr
225                230                235                240

Ser Ala Ile Ser Phe Ala Lys Gly Gly Ser Asp Ala His Leu Ala Gly
                245                250                255

Ala Asn Thr Pro Lys Ala Ala Ala Val Ala Gly Gly Ile Ala Leu Arg
            260                265                270

Ser Leu Val Lys Thr Gly Lys Leu Ala Ala Gly Ala Ala Asp Asn Ala
        275                280                285

Thr Gly Gly Gly Lys Glu Val Gln Gly Val Gly Val Ala Ala Ala Asn
    290                295                300

Lys Leu Leu Arg Ala Val Glu Asp Val Ile Lys Lys Thr Val Lys Asn
305                310                315                320

Val Leu Glu Lys Ala Lys Glu Lys Ile Asp Lys Ala Arg Gly Ser Gln
                325                330                335

Glu Pro Val Ser Glu Ser Ser Lys
            340
```

CLONING AND EXPRESSION OF SOLUBLE TRUNCATED VARIANTS OF BORRELIA OSPA, OSPB AND VMP7

GOVERNMENT SUPPORT

This invention was made with Government support under Contract Number DE-AC02-76CH00016, between the U.S. Department of Energy and Associated Universities, Inc. The Government has certain rights in the invention.

RELATED APPLICATIONS

This Application is a Continuation-in-Part of U.S. application Ser. No. 07/632,072 filed Dec. 21, 1990, now abandoned.

BACKGROUND OF THE INVENTION

Borrelia spirochetes are responsible for a variety of human disorders including Lyme borreliosis and relapsing fevers. Lyme disease is an infection caused by the spirochete, *B. burgdorferi*, which is carried by ticks. The spirochete is transmitted to humans and animals through the bite of a tick and can cause serious dermatological, arthritic, neurological and other pathological disorders in an infected host. Recently, Lyme disease has become a serious epidemiological concern in North America, as well as Europe, Asia and the Soviet Union.

Relapsing fevers are also caused by Borrelia spirochetes and are either tick-borne or louse-borne. Louse-borne relapsing fever is caused by the Borrelia strain *B. recurrentis*, while tick-borne relapsing fevers are caused by any one of a number of Borrelia strains including, in the United States, *B. hermsi*, *B. parkeri* and *B. turicatae*.

It is well documented that persons and animals infected by Borrelia pathogens typically develop antibodies in response to the presence of various Borrelia antigens, including outer membrane lipoproteins. For example, patients infected with Lyme disease develop antibodies to outer surface protein A (OspA), a lipoprotein of the *B. burgdorferi* spirochete. See Craft, J. E., Fischer, D. K., Shimamoto, G. T., and Steere, A. C., "Antigens of *Borrelia burgdorferi* recognized during Lyme disease. Appearance of a new immunoglobulin in response and expansion of the immunoglobulin G response late in the illness," *J. Clin. Invest.*, 78:934–939 (1986). See also, Barbour, A. G., Heiland, R. A., and Howe, T. R., "Heterogeneity of major proteins in Lyme disease borrelia: a molecular analysis of North American and European isolates," *J. Infect. Dis.*, 152:478–484 (1985) The outer surface protein A (OspA) is a lipoprotein encoded by the nucleotide sequence of the ospA gene present in the DNA of the *B. burgdorferi* spirochete. The nucleotide sequence coding for the full-length, wild-type OspA (see SEQ ID NO: 1) has been previously determined for B31, the North American strain of *B. burgdorferi*. See Bergström, S., Bundoc, V. G., & Barbour, A. G., "Molecular Analysis of linear plasmid-encoded major surface proteins, OspA and OspB of the Lyme disease spirochete *Borrelia burgdorferi*," *Mol. Microbiol.*, 3:479–486 (1989). Consequently, the OspA amino acid sequence has been predicted from the nucleotide data (see SEQ ID NO: 2).

Relapsing fever is characterized by repeated episodes of illness and fever separated by periods of well being (see, for example, N. Burman et al., *Mol. Micro.* 4(10):1715–1726 (1990)). The relapsing fever borreliae have developed a mechanism of multiphasic antigenic variation to avoid the immune response of mammalian hosts. The antigenic switch in *B. hermsii* is associated with an outer membrane protein designated 'variable major protein'or Vmp. Vmps of a number of different *B. hermsii* serotypes have been shown to exhibit amino acid sequence variability in many regions of the protein. This sequence variability, or multiphasic antigenic variation, is responsible for the organism's ability to repeatedly escape from the infected host's immune surveillance.

From a clinical standpoint, it is highly desirable to develop a method of producing large quantities of highly purified Borrelia lipoproteins in a soluble form for use in immunoassays and other diagnostic screening tests which detect the presence of antibodies to these proteins in the sera of patients infected with Borrelia spirochetes. Furthermore, soluble, highly purified forms of these lipoproteins would be potentially valuable as clinical immunogens for vaccinating both people and animals against Borrelia pathogens, as well as useful research tools for subsequent laboratory manipulations involving the separation and purification of antibodies to such proteins.

To this end, it is highly desirable to obtain a nucleotide sequence or gene which can be expressed at high levels in a recombinant host/vector expression system to yield large quantities of the resulting recombinant protein while retaining the desired specific reactivity.

Previous attempts have been made to isolate purified, soluble Borrelia lipoproteins through the growth and subsequent purification of Borrelia cell cultures. There are several drawbacks to this approach, however. The growth and subsequent purification of these proteins from crude cell extracts of Borrelia is very time consuming and expensive. Additionally, the growth and manipulation of live Borrelia cultures adds significant risk to laboratory personnel. Most importantly, the full-length, wild-type versions of Borrelia lipoproteins yielded by this method have poor solubility properties because these proteins have a hydrophobic, lipidated character due to their post-translational covalent modification which takes place at the cell membrane of the spirochete during expression. Consequently, detergents are required to solubilize these lipidated proteins.

It is well accepted in the art that the treatment of lipoproteins with detergents improves solubility but often impairs reactivity by altering or destroying the folding configuration of the target protein as well as the epitopic sites. Consequently, it would be desirable to develop a recombinant variation of OspA as well as other Borrelia lipoproteins that are soluble without exposure to detergents while retaining specific reactivity to antibodies against their full-length, wild-type lipoprotein analogs. In addition to the foregoing solubility problems, the association of the Borrelia lipoproteins with the cell membrane of the spirochete also creates problems in the separation and purification of these proteins from crude cell extracts.

As an alternative approach to the production of Borrelia lipoproteins, certain recombinant DNA techniques can be utilized to express Borrelia genes using a host/vector expression system such as *Escherichia coli* containing recombinant cloning vectors known in the art. A suitable recombinant cloning vector would be a plasmid having a nucleotide sequence that could be modified to accept an insertion of wild-type Borrelia DNA. While these recombinant techniques avoid the need for live Borrelia cultures, they have several shortcomings.

For example, recombinant versions of the full-length, wild-type Borrelia lipoproteins produced in *E. coli* have poor solubility properties in the absence of detergents, presumably due to post translational modification of the protein at the cell membrane of the host during expression. Consequently, subsequent manipulations directed to the separation and purification of the resulting protein product involve problems similar to those encountered when attempting to isolate and purify OspA from live *B. burgdorferi* cultures.

Another shortcoming of the above approach is that recombinant versions of the full-length, wild-type ospA and ospB genes are expressed at very low levels in an *E. coli* host. This poor expression is presumably due to the accumulated toxic effects of Borrelia lipoprotein localization at the *E. coli* cell membrane during the course of expression.

SUMMARY OF THE INVENTION

The present invention relates to the discovery that recombinant Borrelia outer surface lipoproteins can be made which are deficient in their signal peptidase II signal sequence and which, as a result of this deficiency, are highly soluble under mild conditions, retain specific antigenic reactivity, and can be expressed at high levels in an appropriate host cell. In particular, the present invention concerns a method for producing recombinant variations of wild-type Borrelia lipoproteins which can be expressed at high levels, and the proteins produced by the method. More particularly, the present invention involves recombinant variations of outer surface protein A (OspA) and outer surface protein B (OspB) of *Borrelia burgdorferi*, and recombinant variations of variable major protein 7 (Vmp7) of *B. hermsii*.

The present invention is a soluble variation of a Borrelia outer surface lipoprotein and a method of producing the same. The soluble recombinant Borrelia outer surface protein can be expressed at high levels in an appropriate host. The amino acid sequence coding for a recombinant variation of OspA is shown in SEQ ID NO: 4. The amino acid sequence coding for a recombinant variation of OspB is shown in SEQ ID NO: 23. The amino acid sequence coding for a recombinant variation of Vmp7 is shown in SEQ ID NO: 24.

The method for providing the protein of the present invention involves producing truncated versions of the wild-type *B. burgdorferi* OspA and OspB, and *B. Hermsii* Vmp7 genes which can be highly expressed in a recombinant host to yield a soluble product. Using a DNA template containing either *B. burgdorferi* or *B. Hermsii* DNA, specially designed oligonucleotide primers were utilized in a polymerase chain reaction to amplify a segment of the wild-type OspA, OspB or Vmp7 gene which excludes sequences encoding a signal peptidase II signal sequence (excludes the first 17 codons of OspA, the first 16 codons of OspB, and the first 27 codons of Vmp7). The resulting amplification product was expressed in a T7 bacteriophage expression system using recombinant DNA techniques known in the art.

The DNA plasmids, pET9-OspA, pET9-OspB and pET9-Vmp7, harboring the nucleotide sequences coding for the variant proteins of the present invention are also provided, in addition to strains of *E. coli* transformed by the same.

The method of the present invention is equally applicable for the production of recombinant variations of other Borrelia lipoproteins.

For a better understanding of the present invention together with other and further objects, reference is made to the following description, taken together with the accompanying drawings.

BRIEF DESCRIPTION OF THE DRAWINGS

FIG. 1 depicts the nucleotide sequence of oligonucleotide primer 201→216 schematically.

FIG. 2 depicts the nucleotide sequence of oligonucleotide primer 958←972 schematically.

FIG. 3 depicts the nucleotide sequence of oligonucleotide primer 151→171 schematically.

FIG. 4 depicts the 5' and 3' ends of the wild-type ospA gene schematically, highlighting the positions where primers 201→216 and 958←972 anneal.

FIG. 5 depicts the 5' and 3' ends of the wild-type ospA gene schematically, highlighting the positions where primers 151→171 and 958←972 anneal.

FIG. 6 schematically depicts the 5' and 3' ends of the product resulting from the amplification of the wild-type ospA gene by primer 201→216 and primer 958←972.

FIG. 10 is a photograph of a SDS-12.5% PAGE gel stained with Coomassie blue upon which various cellular protein samples were run subsequent to removal from induction at specified time intervals.

FIG. 11 is a photograph of a SDS-PAGE gel upon which uninduced cells were compared with induced cells sampled at one hour intervals after induction.

FIG. 12 is a photograph of a SDS-PAGE gel upon which OspA samples were run. The samples were taken at different stages of purification.

FIG. 14 is a photograph of a SDS-12.5% PAGE gel stained with Coomassie blue upon which proteins from cells carrying pET9-preOspA and cells carrying pET9-OspA were compared to proteins from whole *B. burgdorferi* cells.

FIG. 15 is an autoradiogram of the gel photographed in FIG. 14.

FIG. 16 is an autoradiogram of the nitrocellulose blot of the gel photographed in FIG. 14 before further Western analysis.

FIG. 17 is an autoradiogram of the nitrocellulose blot of the gel photographed in FIG. 14 after probing with antibodies.

FIG. 18 is a photograph of the completed Western blot of the gel photographed in FIG. 14 after treatment with alkaline phosphatase color developing reagents.

FIG. 19a depicts the nucleotide sequence of oligonucleotide primer #1104 schematically.

FIG. 19b depicts the nucleotide sequence of oligonucleotide primer #1105 schematically.

FIG. 19c depicts the nucleotide sequence of oligonucleotide primer #1106 schematically.

FIG. 20a depicts the nucleotide sequence of oligonucleotide primer Vmp7-2 schematically.

FIG. 20b depicts the nucleotide sequence of oligonucleotide primer Vmp7-3 schematically.

FIG. 21a depicts the 5' and 3' ends of the wild-type ospB gene schematically, highlighting the positions where primers #1104, #1105 and #1106 anneal.

FIG. 21b depicts the 5' and 3' ends of the wild-type ospB gene schematically, highlighting the positions where primers #1104, #1105 and #1106 anneal, and depicting the additional sequence provided by the primer #1105.

FIG. 21c schematically depicts the 5' and 3' ends of the product resulting from the amplification of the wild-type ospB gene by primer #1104 and primer #1106, highlighting the positions where these primers anneal.

FIG. 22a depicts the 5' and 3' ends of the wild-type Vmp7 gene schematically, highlighting the positions where primers Vmp7-2 and Vmp7-3 anneal.

FIG. 22b schematically depicts the 5' and 3' ends of the product resulting from the amplification of the wild-type Vmp7 gene by primer Vmp7-2 and Vmp7-3, highlighting the positions where these primers anneal.

FIG. 26 depicts the nucleotide sequence and the amino acid sequence of the translation product of the wild-type ospA gene, SEQ ID NO: 1.

FIG. 27 depicts the nucleotide sequence and the amino acid sequence of the translation product of the soluble variant ospA gene, SEQ ID NO: 3.

FIG. 28 depicts the nucleotide sequence and the amino acid sequence of the translation product of the soluble variant ospB gene, SEQ ID NO: 21.

FIG. 29 depicts the nucleotide sequence and the amino acid sequence of the translation product of the soluble variant of the Vmp 7 gene, SEQ ID NO: 22.

DETAILED DESCRIPTION OF THE INVENTION

Figure 7:
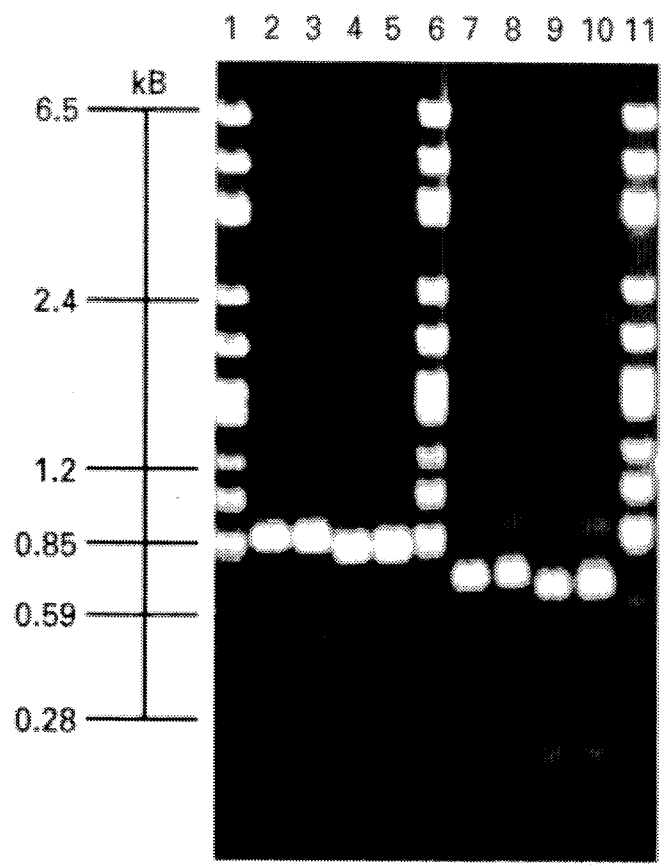
FIG. 7 is a photograph of a one percent agarose gel stained with ethidium bromide upon which amplification products were run.

The present invention relates to the discovery that redesigning a wild-type Borrelia outer surface lipoprotein gene to encode an inactive or deleted lipidation signal yields a recombinant variation of a Borrelia outer surface lipoprotein which can be expressed at high levels in an appropriate host. This recombinant variation was further found to be readily soluble without exposure to detergents and to retain a selective reactivity to antibodies against the wild-type Borrelia outer surface lipoprotein. It is the presence of the intact lipidation signal which has accounted for the shortcomings in prior art attempts to produce soluble recombinant forms Borrelia outer surface lipoproteins that are highly expressed in *E. coli*.

More precisely, within the region encoding the leader sequences of wild-type *B. burgdorferi* outer surface proteins A and B, and *B. hermsii* variable major protein 7, there is a signal which triggers lipidation of the resulting protein (the leader sequences comprising the first 17 codons of OspA, SEQ ID NO: 1, the first 16 codons of OspB, SEQ ID NO: 19 and FIG. 21a, and the first 27 codons of Vmp 7, SEQ ID NO: 20 and FIG. 22a). The resulting lipidation impairs both the solubility of the wild-type protein as well as the expression and processing of the wild-type protein within a host bacterium such as *E. coli*. Herein described is a method for inactivating the signal which triggers the lipidation. It is to be understood that although the method disclosed in the following Examples describes deletion of the lipidation signal and lipidation site, inactivation of the signal alone would be sufficient to prevent the undesirable effects caused by lipidation of a protein.

The proteins of the present invention are highly advantageous in that they retain specific reactivity to antibodies against wild-type Borrelia lipoproteins while maintaining improved solubility properties over wild-type proteins derived from live cultures or from other recombinant techniques. This improved solubility is particularly useful in immuno-diagnostic assays as well as in laboratory manipulations because the protein is soluble in the absence of detergents or other harsh conditions which can impair or destroy specific antigenicity. For example, proteins of the present invention can be used as highly purified reagents in ELISA assays to detect the presence of antibodies to native Borrelia in potentially infected individuals. These proteins can also be used as immunodiagnostic reagents in dot blots or western blots.

Another advantage of the proteins of the present invention is that, unlike wild-type or recombinantly expressed wild-type Borrelia outer surface lipoproteins, the recombinant proteins herein described are not associated with the host cell membrane during expression. As a consequence, the proteins of the present invention can be expressed to high levels because they are not toxic to the host organism as would be a membrane-associated foreign protein. Improved recombinant expression affords high yields of the target protein while obviating the risks and expenses of live Borrelia cell cultures.

A further advantage of the present invention is that it provides a method of producing a recombinant variation of Borrelia lipoproteins which are expressible at high levels in an appropriate host and which have improved solubility in the absence of detergents while retaining specific reactivity to antibodies directed against their wild-type lipoprotein analogs. Prior to the method of the present invention, detergents or other harsh treatments were required to solubilize these lipoproteins for use in immunoassays and other laboratory manipulations thereby exposing the protein and its antigenic sites to potential damage.

In addition, proteins of the present invention are good candidates for vaccine immunogens against Borrelia infections. Recent studies have shown that *Borrelia burgdorferi* sonicates possess a mitogen which is able to stimulate directly lymphocytes from naive (previously unexposed) mice or humans to proliferate vigorously (Schoenfeld, R., et al. "Demonstration of a B-Lymphocyte Mitogen Produced by the Lyme Disease Pathogen, *Borrelia burgdorferi*" *Infect. Immun.* 60:455–464 (1992)). Furthermore, *B. burgdorferi* sonicates can stimulate activation of immunoglobulin production by normal B lymphocytes. It has been speculated that such activation could lead to the appearance of autoreactive antibodies which may play a significant role in the pathogenesis of Lyme disease. A lipoprotein from the outer membrane of *E. coli* is known to be a potent B-cell mitogen and polyclonal B-cell activator, and it is generally believed that these stimulatory properties are due in a large part to the covalently attached lipid at the amino-terminus of the protein. While the precise biochemistry of the *B. burgdorferi* mitogen is currently unknown, there is concern that covalently bound lipid may constitute part of the nonspecific stimulatory activity associated with *B. burgdorferi*. Therefore, the proteins or immunogens or DNA of the present invention would be advantageous as vaccines because such vaccines would avoid the potential risk of stimulating a pathological autoimmune response, which risk may otherwise attend the administration of wild-type Borrelia outer surface lipoproteins.

For the purpose of understanding the present invention, the following terms are defined:

Bacteria are prokaryotic organisms that possess a tough protective coat known as a cell wall beneath which a cell membrane encloses a single cytoplasmic compartment containing DNA, RNA, proteins and small molecules. Examples include spirochetes and *Escherichia coli*.

A codon is a nucleotide triplet encoding a single amino acid.

High level of expression is a high level as compared to the level of expression attainable with recombinant wild-type Borrelia lipoproteins. For example, the bacteriophage T7 RNA polymerase can direct high level transcription from a T7 promoter on a multicopy plasmid, efficiently transcribing almost any DNA linked to a T7 promoter. If there are no other bars to efficient post-transcriptional processing of the protein product, then this results in high level expression of the linked DNA.

The term lipoprotein as used herein encompasses: 1) a protein having a signal peptidase II signal sequence; and 2) a protein which has a signal peptidase II signal sequence and is lipidated.

A soluble variant or variation of a Borrelia outer surface lipoprotein as described herein is the protein having the amino acid sequence of a Borrelia outer surface lipoprotein which lacks the signal peptidase II signal sequence present in the corresponding wild-type Borrelia lipoprotein (i.e., all or a portion of the signal peptidase II signal sequence has been deleted) or which has an inactivated (nonfunctional) signal peptidase II signal sequence and, as a result, is not lipidated.

A highly expressed recombinant is highly expressed in comparison with the level of expression of the wild-type recombinant. A recombinant soluble variant as described herein is generally expressible at high levels.

A plasmid is a double-stranded, closed, circular DNA molecule independent of the chromosome and comprising an intact replicon such that the plasmid is replicated in a host cell. When the plasmid is placed within a cell, the characteristics of the organism may be altered. For example, a plasmid may confer resistance to certain antibiotics.

Primer refers to an oligonucleotide (a short nucleic acid chain), which is capable of acting as a point of initiation of DNA synthesis or polymerization when placed under conditions in which synthesis of a primer extension product, which is complementary to a nucleic acid strand, is induced. The primer may occur naturally, for example as in a purified restriction digest product, or it may be produced synthetically.

While the method of the present invention is illustrated in terms of constructing recombinant variations of *B. burgdorferi* OspA and OspB, and *B. Hermsii* Vmp 7, the method is equally applicable to other Borrelia lipoproteins.

Construction of a Soluble Variant of *B. burgdorferi* OspA

The production of a truncated nucleotide sequence (see SEQ ID NO: 3) coding for a preferred embodiment of the recombinant variation of OspA (see SEQ ID NO: 4) is generally provided for as illustrated below and in Examples 1–7. All techniques and materials used to construct and express the OspA variant are the same as those used to construct and express the OspB and Vmp7 variant lipoproteins, except that the oligonucleotide primers used to construct variant OspB and Vmp7 are different than those used to construct variant OspA. The primers used to construct soluble variant OspB and Vmp7 proteins, and the results obtained with those variants, are described in Examples 8–10.

DNA containing the full-length, wild-type *B. burgdorferi* (B31 strain) ospA gene was isolated and purified. A set of oligonucleotide primers (see SEQ ID NO: 11/FIG. 1 and SEQ ID NO: 12/FIG. 2) was synthesized for use in the polymerase chain reaction (PCR) allowing for the specified amplification of a truncated version of the ospA gene lacking the first 17 codons. Use of these primers also resulted in the inclusion of preferred restriction sites before and after the coding sequence of the amplified product. A second set of oligonucleotide primers (see SEQ ID NO: 13/FIG. 3 and SEQ ID NO: 12/FIG. 2) was also synthesized for use in the PCR to allow for the specified amplification of the entire wild-type ospA gene for use as a control in the following examples.

The resulting DNA fragments produced by the PCR were purified and selected by restriction site analysis and subsequently subcloned into an appropriate plasmid expression vector. The resulting expression vectors were then transferred to a host expression strain for protein production.

EXAMPLE 1

Template DNA and Oligonucleotide Primers used for Constructing a Recombinant, Soluble Variant of *B. Burgdorferi* OspA Gene In order to construct the protein of the present invention, it was necessary to procure a source of wild-type *B. burgdorferi* DNA containing the nucleotide sequence coding for OspA. This DNA served as a template for the amplification of the desired segment of the wild-type, ospA gene (see SEQ ID NO: 1) during the PCR. It is well known in art that starting material for recombinant DNA manipulations can be DNA isolated from cultures of the wild-type organism of interest, and the starting material can also come from recombinant DNA, such as plasmids, that have been genetically engineered to contain cloned copies of the target DNA. The latter approach is advantageous because it promotes homogeneity of the resulting clones and reduces the frequency of mutation in the DNA fragment of interest, and because enhanced amounts of a DNA of interest can be produced relative to other host DNA.

In a preferred method of producing a protein of the present invention, the initial source of template DNA containing the full-length, wild-type ospA gene was a recombinant clone of the ospA gene obtained from a previously engineered plasmid, pTRH44. The plasmid pTRH44, having a 1.6-kb restriction fragment containing the full-length, wild-type *B. burgdorferi* ospA gene cloned into pUC9, has been previously described. See Howe, T. R., LaQuier, F. R., and Barbour, A. G., "Organization of genes encoding two outer membrane proteins of the Lyme disease agent *Borrelia burgdorferi* within a single transcriptional unit," *Infec. Immun.*, 54:207–212 (1986)

Alternatively, total *B. burgdorferi* DNA could have been isolated and purified by phenol extraction of lysozyme-proteinase K-SDS extracts of Borrelia cells. Techniques for isolation and purification of template DNA from total DNA extracts are generally well known in the art. For example, see Howe, T. R., Mayer, L. W., and Barbour, A. G., "A single recombinant plasmid expressing two major outer surface proteins of the Lyme disease spirochete," *Science* 227:645–646, (1985). For examples on cultivation and isolation of *B. burgdorferi* see Barbour, A. G., "Isolation and cultivation of Lyme disease spirochetes," *Yale J. Biol. Med.*, 57:521–525 (1984).

A first and second set of oligonucleotide primers were synthesized in a Microsyn 1450 DNA synthesizer (available from Systec, Minneapolis, Minn.). The resulting products were subsequently purified using Poly-Pak® purification cartridges (obtained from Glen Research Corporation, Herndon, Va.) according to the manufacturer's specifications. DNA synthesis and subsequent purification techniques are well known in the art of recombinant DNA technology. Any suitable techniques for achieving these steps would be acceptable.

The first set of oligonucleotide primers was designed for the amplification of a nucleotide sequence coding for a recombinant variation of *B. burgdorferi* OspA while the second set of primers was designed for the amplification of the entire wild-type *B. burgdorferi* ospA gene. Each primer contained a 5' end and a 3' end. The 3' end of each primer contained a region having a nucleotide sequence complementary to a specific sequence of nucleotides appearing at a particular segment of the wild-type *B. burgdorferi* ospA gene present within the *B. burgdorferi* genome. It was this region of the primer that annealed to the *B. burgdorferi* DNA template to promote polymerization during the PCR. The nucleotide sequence for the wild-type ospA gene (see SEQ ID NO: 1) has been previously determined. See Bergström, S., Bundoc, V. G., and Barbour, A. G., "Molecular Analysis of linear plasmid-encoded major surface proteins, OspA and OspB, of the Lyme disease spirochete *Borrelia burgdorferi*," *Mol Microbiol.*, 3:479–486 (1989).

The 5' end of each primer contained a nucleotide sequence that was non-complementary to the *B. burgdorferi* DNA template and introduced unique restriction sites in the DNA fragments produced during PCR amplification. These unique restriction sites facilitated the cloning of the resulting fragments into an expression vector. The use of restriction sites to facilitate cloning is well known in recombinant DNA technology.

The first set of oligonucleotide primers included a first and a second primer. The first primer was denoted as primer 201→216 and was synthesized to yield the nucleotide sequence (SEQ ID NO: 11) shown in FIG. 1. The numbers 201–216 indicate the specific nucleotide positions on the full-length, wild-type ospA gene to which the primer was complementary. Referring to FIG. 1, the under-lined region indicates the segment of the primer which was complementary to the full-length, wild-type ospA gene at nucleotide positions 201 through 216. The nucleotides appearing in boldface print indicate a restriction site recognized by the restriction enzyme NdeI. The slash mark represents the site where the NdeI enzyme later cleaved the strand to facilitate cloning into the expression vector.

Primer 201→216 was used to alter the 5' end of the wild-type OspA gene, producing a truncated ospA gene (the nucleotide sequence coding for the recombinant variation of OspA) and providing a NdeI restriction site. DNA encoding the truncated OspA protein was obtained by PCR amplification from the full-length, wild-type ospA gene, using Primer 201→216 to initiate polymerization at the 18$^{th}$ codon. In the wild-type version of the ospA gene, a potential recognition site for lipoprotein signal peptidase II occurs between the 16$^{th}$ and 17$^{th}$ codon.

The exact mechanism for lipidation of full-length, wild-type OspA within the Borrelia spirochete is not known. However, it is now generally accepted in the art that the amino acid sequence Leu-x-y-Cys (where x and y generally are different amino acids having non-polar side chains), appearing in the leader sequence of certain bacterial lipoproteins, codes for a processing signal to initiate protein processing by the bacterial enzyme, signal peptidase II. This enzyme is ultimately responsible for cleaving the N-terminal portion of the leader sequence at the amino end of the cysteine residue, leaving the N-terminal cysteine to be covalently linked to fatty acids which give the remaining protein a highly lipidated character upon attachment. Many prokaryotic cells such as *E. coli* utilize the foregoing processing scheme to process and transfer their own cellular lipoproteins to the membrane of the cell. See Bergström, S., Bundoc, V. G., and Barbour, A. G., "Molecular Analysis of linear plasmid-encoded major surface proteins, OspA and OspB, of the Lyme disease spirochete *Borrelia burgdorferi*," *Mol. Microbiol.*, 3:479–486 (1989). See also Brandt, M. E., Riley, B. S., Radolf, J. D., and Norgard, M. V., "Immunogenic integral membrane proteins of *Borrelia burgdorferi* are lipoproteins," *Infect. Immun.*, 58:983–991 (1990).

Although the entire amino acid sequence of the wild-type version of *B. burgdorferi* OspA has not been confirmed by amino acid analysis due to problems inherent in the protein, the sequence has previously been predicted based upon the known nucleotide sequence of the full-length, wild-type *B. burgdorferi* (B31) ospA gene. See Bergström, S., Bundoc, V. G., and Barbour, A. G., "Molecular Analysis of linear plasmid-encoded major surface proteins, OspA and OspB, of the Lyme disease spirochete *Borrelia burgdorferi*," *Mol Microbiol*, 3:479–486 (1989). SEQ ID NO: 2 illustrates the predicted amino acid sequence of the full-length, wild-type *B. burgdorferi* OspA as previously deduced.

Referring to SEQ ID NO: 2, it can be seen that the leader portion of the predicted amino acid sequence contains a segment having the consecutive amino acid residues Leu-Ile-Ala-Cys. These residues conform to the format of the processing signal for signal peptidase II in *E. coli*, as mentioned above. Thus in the wild-type version of the ospA gene, a potential recognition site for lipoprotein signal peptidase II occurs between the 16$^{th}$ and 17$^{th}$ codon due to the sequence homology between the known signal sequence format for signal peptidase II and the potential signal sequence appearing in the predicted amino acid sequence of the full-length, wild-type *B. burgdorferi* OspA.

To increase the likelihood that the resulting recombinant protein would not become lipidated during expression, the complementary segment of primer 201→216 was designed to exclude the cysteine residue and to initiate amplification at the portion of the *B. burgdorferi* wild-type ospA gene beginning at the 18$^{th}$ codon. This OspA variant completely eliminates the potential recognition site for lipidation. It was hoped that the elimination of this potential recognition site would increase solubility and improve expression of the resulting protein without impairing specific reactivity to antibodies against wild-type *B. burgdorferi* OspA.

Prior to the present invention, it was not known whether the potential signal sequence appearing in the amino acid sequence of wild-type *B. burgdorferi* OspA was responsible for the lipidation of the mature protein. It was further unknown whether the potential signal sequence would be involved in a similar lipidation of a recombinant version of wild-type OspA produced in a recombinant host. It was yet further unknown whether the elimination of a portion of the wild-type ospA gene containing the potential signal sequence would result in a truncated ospA gene which could be effectively expressed using recombinant methods to yield a protein having improved solubility in the absence of detergents while retaining reactivity to antibodies against the wild-type version of the protein.

Referring to FIG. 1, a preferred construction of primer 201→216 called for a non-complementary segment (GCT), coding for an alanine residue, to be positioned between the complementary segment of the primer and the NdeI restriction site. The NdeI restriction site positioned within primer 201→216 included a triplicate (ATG) coding for methionine, a terminal amino acid residue which functions as an initiation site during protein production. The triplicate coding for alanine was added because alanine is one of the amino acids which facilitates the efficient removal of the amino-terminal methionine from the final protein product. Other amino acids suitable for facilitating the removal of methionine would also be acceptable. For example, it is known that glycine, proline, serine, valine and threonine are also particularly efficient at facilitating the removal of the N-terminal methionine. See Hirel, P-H., Schmitter, J-M., Dessen, P., Fayat, G., and Blanquet, S., "Extent of N-terminal methionine excision from *Escherichia coli* proteins is governed by the side-chain length of the penultimate amino acid," *Proc. Natl. Acad, Sci, U.S.A.*, 86:8247–8251 (1989). It is generally known that methionine appearing at the terminal end of an amino acid sequence for the purpose of translation initiation is not important to the characteristics of the resulting protein and is usually removed from the amino acid sequence.

In a preferred form of the present invention, the amino acid sequence resulting from the recombinant truncated ospA gene had an additional alanine residue at the amino terminal end. Since the first 17 codons were eliminated from the truncated version of the ospA gene, the nucleotide triplicate coding for the alanine residue was positioned to precede the nucleotide triplicate coding for a lysine residue at what would be the $18^{th}$ codon in the wild-type ospA gene. Methionine was removed in the mature form of the expressed protein. The resulting amino acid sequence with methionine removed is illustrated in SEQ ID NO: 6. The corresponding nucleotide sequence is shown in SEQ ID NO: 5.

Alternatively, the additional alanine residue could have been left out. The resulting amino acid sequence including the initiating methionine is illustrated in SEQ ID NO: 8. The corresponding nucleotide sequence is shown in SEQ ID NO: 7. Removal of methionine results in amino acid sequence SEQ ID NO: 10. The corresponding nucleotide sequence is shown in SEQ ID NO: 9. In another form of the present invention, DNA sequence encoding additional amino acids could be inserted between the amino-terminal methionine and the wild-type sequence downstream from the signal peptidase II signal sequence.

The second primer was denoted as primer 958←972 and was synthesized to yield the sequence (see SEQ ID NO: 12) shown in FIG. 2. Referring to FIG. 2, the underlined region of the primer indicates the segment which was complementary to the wild-type ospA gene at positions 958 through 972 while the nucleotides appearing in boldface print indicate a restriction site recognized by restriction enzyme BglII. The slash mark represents the site where the BglII enzyme later cleaved the product strand to facilitate cloning into the expression vector. Referring to SEQ ID NO: 12, it can be seen that the entire sequence is shown in a noncoding format as contrasted with the format presented in SEQ ID NOS: 11 and 13, which correspond to primer 201→216 and primer 151→171, respectively. The noncoding format was used because the sequence of primer 958←972 is designed to prime the amplification of the non-sense strand of the ospA gene rather than the sense strand.

Primer 958←972 was common to both sets of oligonucleotide primers. Insofar as the first set of primers was concerned, primer 958←972 was used to redesign a 3' end for the truncated ospA gene providing a BglII restriction site and priming the amplification in a direction antiparallel to the direction of amplification directed by primer 201→216.

Referring to FIG. 4, the wild-type ospA gene is depicted schematically. (The sequence of the wild-type OspA gene is depicted at SEQ ID NO: 1 and FIG. 26.) The two regions of nucleotides underlined highlight the positions where primer 201→216 and primer 958←972 annealed to the template DNA to promote amplification. The arrowheads denote the direction of polymerization initiated by the primer which annealed at the position indicated.

The second set of oligonucleotide primers, designed for the amplification of the entire wild-type *B. burgdorferi* ospA gene as a control, also included a first and a second primer. The first primer was denoted as primer 151→171 and was synthesized to yield the nucleotide sequence (see SEQ ID NO: 13) shown in FIG. 3. Referring to FIG. 3, the underlined region indicates the segment of the primer which was complementary to the wild-type ospA gene at nucleotide positions 151 through 171. The nucleotides appearing in boldface print indicate a restriction site recognized by restriction enzyme NdeI. The slash mark indicates the site where the NdeI enzyme later cleaved the product strand to facilitate cloning into the expression vector.

The second primer, primer 958←972, was common to both sets of oligonucleotides as previously mentioned. Insofar as the second set of primers was concerned, primer 958←972 introduced a BglII restriction site and primed the amplification of the wild-type ospA gene in a direction antiparallel to the direction of amplification directed by primer 151→171.

Referring to FIG. 5, the wild-type ospA gene is depicted schematically. The two regions of nucleotides underlined highlight the positions where primer 151→171 and primer 958←972 annealed to promote amplification. The arrowheads denote the direction of polymerization initiated by the primer which annealed at the position indicated.

FIG. 6 is a schematic illustration of the product resulting from the amplification of the truncated version of the ospA gene from the wild-type ospA gene by primer 201→216 and primer 958←972. The boldface print denotes the restriction sites provided by the primers while the underlined regions indicate the section of the primer which annealed to the wild-type ospA gene prior to amplification. FIG. 27 depicts the nucleotide sequence and the amino acid sequence of the translation product of the variant OspA gene, SEQ ID NO: 3.

The basic methods for amplifying a desired target nucleic acid sequence using oligonucleotide primers are generally known in the art and are illustrated in U.S. Pat. No. 4,683, 202 to Mullis and U.S. Pat. No. 4,800,159 to Mullis, et al., both of which are incorporated herein by reference. For additional information concerning cloning techniques, see Maniatis, T., Fritsch, E. F., and Sambrook, J., *Molecular Cloning: A Laboratory Manual*, Cold Spring Harbor Laboratory, Cold Spring Harbor, N.Y. (1982). See also, Ausubel, F. M., Brent, R., Kingston, R. E., Moore, D. D., Seidman, J. G., Smith, J. A., and Struhl, K., *Current Protocols in Molecular Biology*, John Wiley & Sons, New York, N.Y. (1989).

Utilizing primers 151→171, 201→216 and 958←972, polymerase reaction amplifications were carried out in 50μl reaction volumes containing 1 unit AmpliTaq DNA polymerase (obtained from Perkin-Elmer Cetus, Norwalk, Conn.), each primer at 1μM and ≈0.1μg template DNA. The reaction mix also contained 10 mM Tris-HCl (pH8.0), 50 mM KCl, 1.5 mM $MgCl_2$, 0.05% Tween 20, 0.05% Nonidet P-40, 0.26 mM dATP, 0.26 mM dTTP, 0.14 mM dCTP and 0.14 mM dGTP.

In a preferred method of amplification, the dNTP concentrations used reflected the known DNA base content of 29% G+C for *B. burgdorferi* to eliminate the possibility of undesirable mutations. See Schmid, G.P., Steigerwalt, A. G., Johnson, S., Barboug, A. G., Steere, A. C., Robinson, I. M. and Brenner, D. J., "DNA characterization of Lyme disease spirochetes," *Yale J. Biol. Med.*, 57:539–542 (1984).

Before amplification, the reaction was overlaid with mineral oil and amplification was carried out for 25 cycles in a DNA Thermal Cycler (obtained from Perkin-Elmer Cetus, Minneapolis, Minn.) with each cycle consisting of 1 minute at 94° C., 1 minute at 47° C. and 3 minutes at 72° C. Amplification was completed by a final incubation at 72° C. for 10 minutes. The amplified products were extracted with phenol, ethanol precipitated, cleaved with the appropriate restriction enzymes and then purified by electrophoresis on 1% low melting point agarose gels (obtained from Bethesda Research Laboratories, Gaithersburg, Md.). Other techniques known in the art for purification of amplified DNA products, such as electrophoresis on acrylamide gels, would be acceptable.

The amplification products were run on a 1% agarose gel, stained with ethidium bromide and photographed with ultraviolet illumination. Referring to FIG. 7, Lanes 1 6 and 11 contain HaeII digested T7 DNA as molecular length markers. Sizes are in kilobase pairs (kB). Lanes 2, 4, 7 and 9 contain 1/5 volume of the products of the reactions with total *B. burgdorferi* DNA while lanes 3, 5, 8 and 10 contain 1/50 volume of the reaction mix resulting from amplification using plasmid pTRH44 (containing the full-length, wild-type *B. burgdorferi* ospA gene cloned into pUC9) as a template. The samples applied were generated using primers that amplify the entire ospA coding sequence (Lanes 2, 3, 7 and 8 ) or the region beginning at $Lys^{18}$ (Lanes 4, 5, 9 and 10 ). As shown in Lanes 7–10, the amplified DNA can be cut with EcoRI to give products with the mobilities expected from cutting at the single EcoRI site in ospA (662+182, and 623+182 bps, respectively).

EXAMPLE 2

Construction of the OspA Expression Vector

Figure 8:
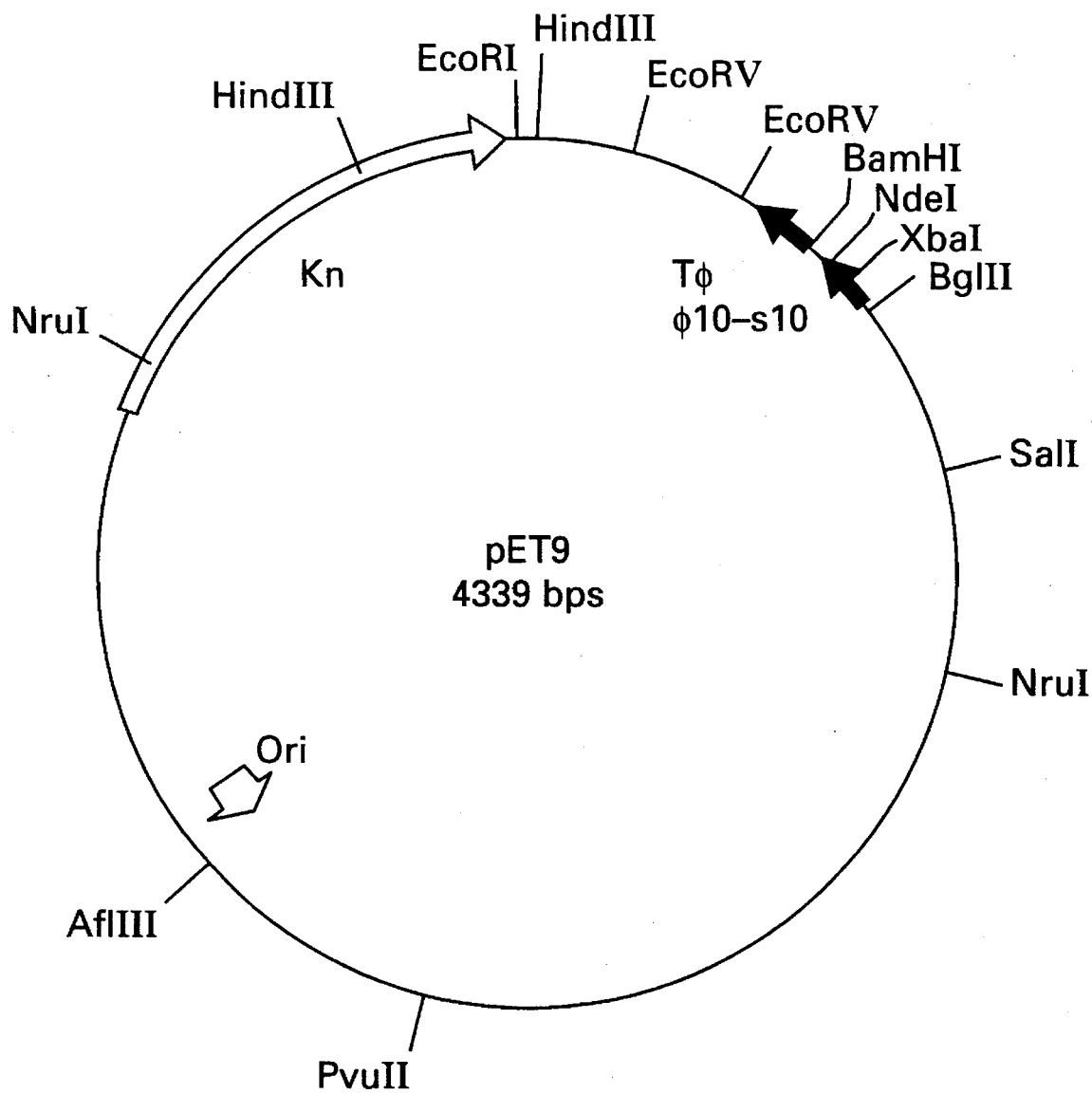
FIG. 8 is a schematic representation of plasmid pET9.

In order to express the amplified version of the truncated ospA gene as well as the amplified version of the full-length, wild-type ospA gene, the DNA fragments resulting from amplification by the PCR were ultimately cloned into a plasmid vector for protein production. A preferred plasmid vector for protein production in the present invention is pET9 in which the ospA gene is placed under control of a T7 promoter and efficient translation initiation signals from bacteriophage T7. The pET9 expression plasmid is schematically depicted in FIG. 8. The pET9 and pLysS expression vectors, the bacterial hosts for cloning, growth media and the methods used to direct expression of cloned genes by T7 RNA polymerase have previously been described. See Studier, F. W., Rosenberg, A. H., Dunn, J. J. and Dubendorff, J. W., "Use of T7 RNA polymerase to direct expression of cloned genes," *Meth . Enzymol.* 185:60–89 (1990). Cloning and expression of the gene for bacteriophage T7 RNA polymerase is also presented in U.S. Pat. No. 4,952,496 to Studier, et al., incorporated herein by reference. While a T7 promoter system is a preferred expression system in the present invention, expression of the truncated ospA gene is not to be so limited with respect to expression format, provided that the expression system of choice is compatible with the host organism employed for expression.

The resulting plasmids were designated as pET9-preOspA, denoting the plasmids which received the amplified DNA fragment coding for the full-length, wild-type OspA used as a control, and pET9-OspA, denoting the plasmids which received the amplified DNA product coding for the recombinant truncated variation of OspA. These two plasmids are depicted schematically in FIG. 9a (pET9-preOspA) and FIG. 9b (pET9-OspA).

In a preferred form of the present invention, the pET9 vector harbored the kan gene (conferring kanamycin resistance to the host organism) as its selective marker instead of a bla gene (which would have conferred resistance to ampicillin to the host organism). consequently, ampicillin is not used during cell growth and, therefore, there is no possibility that an immunogenic ampicilloyl/OspA target protein conjugate can be formed. Conjugates of this type are believed to be major antigenic determinants in penicillin allergy and their presence could complicate projected immunological studies. See Yvon. M., Anglade, P., and Wal, J.-M., "Identification of the binding sites of benzyl penicilloyl, the allergenic metabolite of penicillin, on the serum albumin molecule," FEBS, 263:237–240 (1990). A schematic representation of pET9 and pET9-OspA plasmids are shown in FIGS. 8 and 9, respectively.

Plasmids pET9-preOspA and pET9-OspA were initially cloned into the *E. coli* strain DH5α, a host that lacks T7 RNA polymerase. Background expression is minimal in this host because the bacterial RNA polymerase does not initiate transcription from the T7 promoter. This feature allows stable recombinant plasmids to be established in this host even though the product of the gene introduced on the plasmid vector is toxic to *E. coli*. The correctness of the resulting plasmids was confirmed by extensive restriction site analysis and standard dideoxy sequencing of the entire ospA coding sequences.

Although the primers used here were specifically designed to amplify certain segments of the wild-type ospA sequence from total *B. burgdorferi* DNA, for practical reasons and because the mutation probability increases with the number of amplification cycles, the plasmids used in the present invention were constructed using NdeI/BglII fragments obtained from reactions containing the ospA plasmid, pTRH44, as a DNA template. Subsequently, the resulting 824 and 779 bp NdeI/BglII fragments from each reaction were subcloned separately into the T7 expression vector pET9 which had been digested with NdeI and BamHI, dephosphorylated and purified by electrophoresis on 1% low melting point gels. The plasmid pTRH44 having a 1.6-kb restriction fragment containing full-length, wild-type ospA gene cloned into pUC9 has been previously described. See Howe, T. R., LaQuier, F. R., and Barbour, A. G., "Organization of genes encoding two outer membrane proteins of the Lyme disease agent *Borrelia burgdorferi* within a single transcriptional unit," *Infec. Immun.*, 54:207–212 (1986).

Figure 9A:
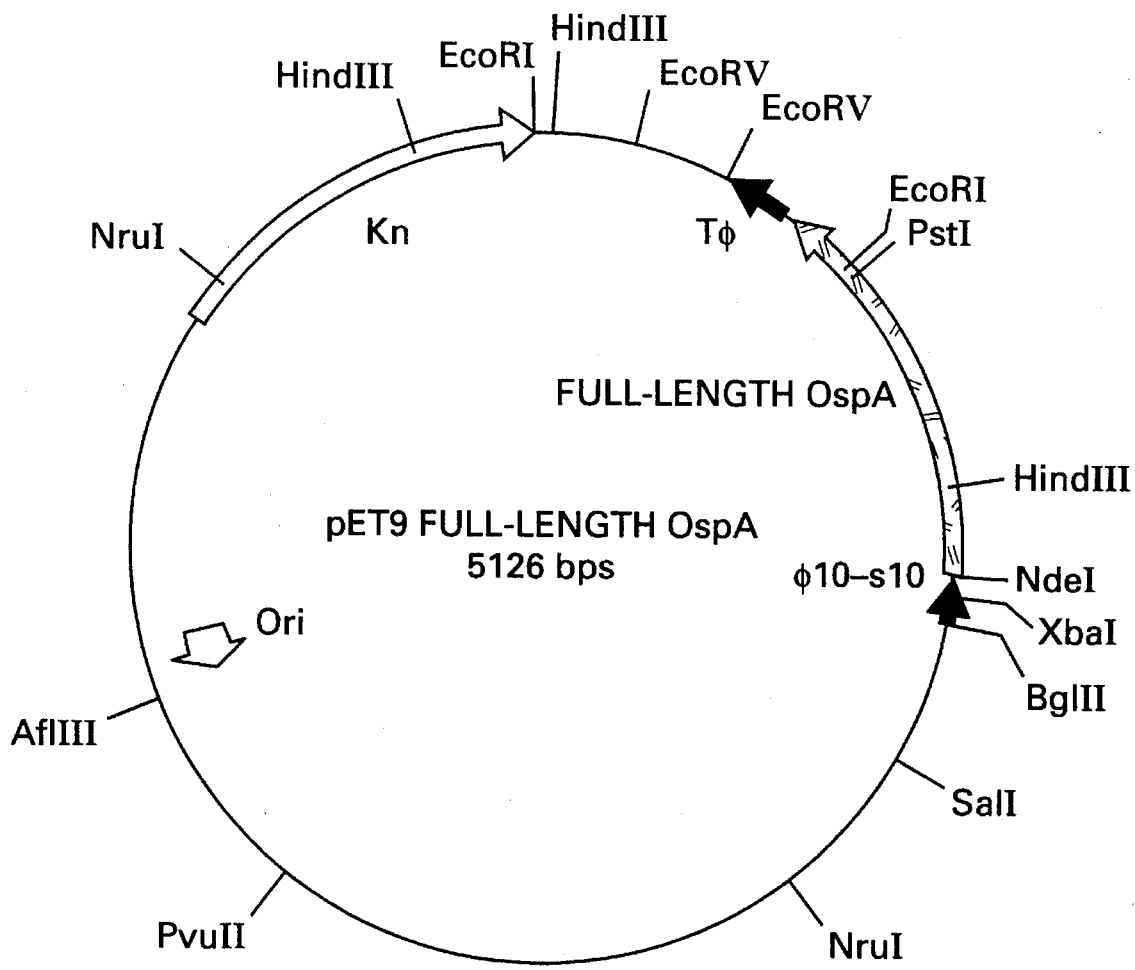
FIG. 9a is a schematic representation of plasmid pET9-preOspA.
Figure 9B:
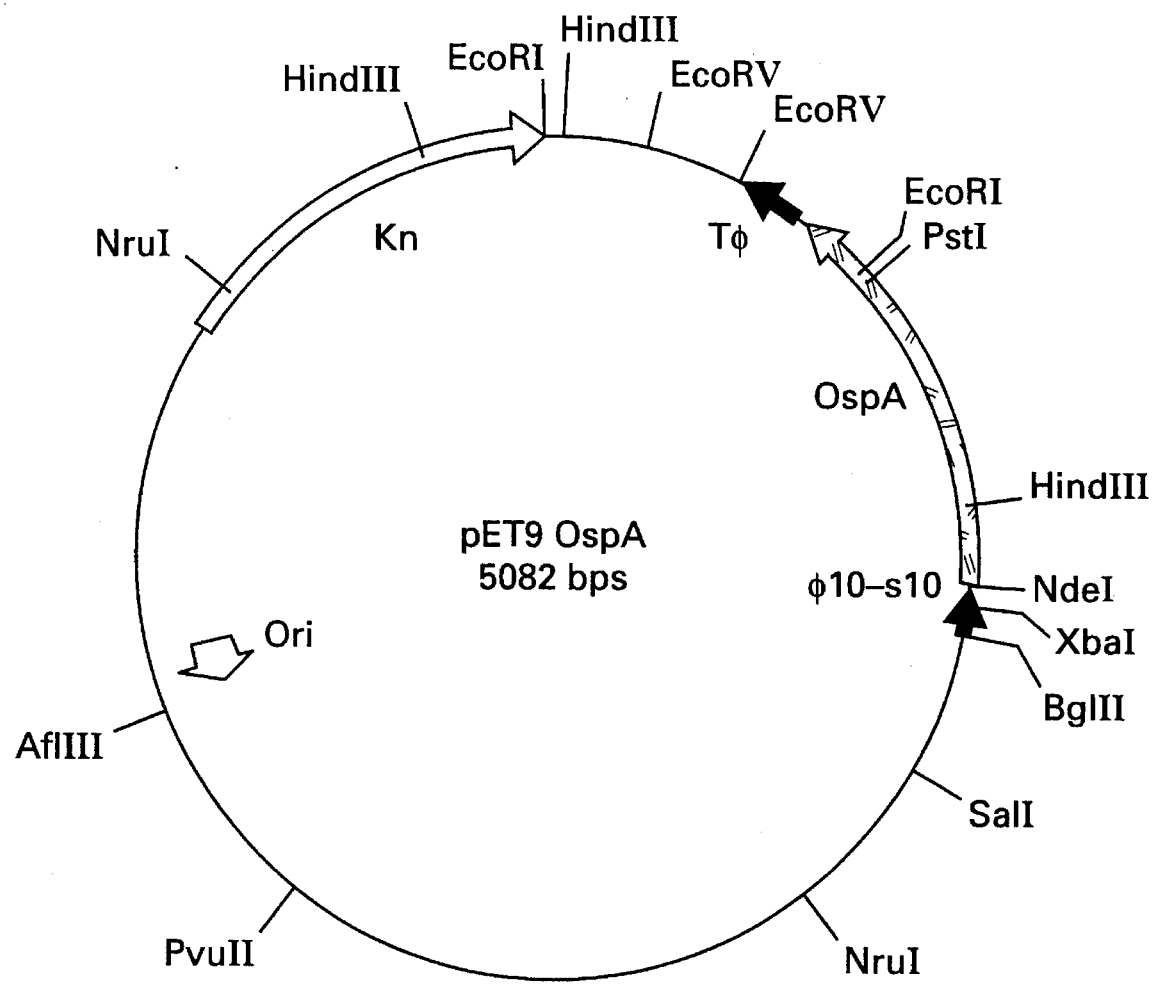
FIG. 9b is a schematic representation of plasmid pET9-OspA.

Referring to FIGS. 8 and 9, digestion of the amplified DNAs with NdeI/BglII and subsequent ligation into NdeI/BamHI-digested pET9 produced pET9-preOspA and pET9-OspA, which are 5127 and 5082 bps, respectively. φ10-S10 represents φ10 promoter for bacteriophage T7 RNA polymerase and the ribosome binding and translational start site for T7 gene 10. Tφ is the transcriptional termination signal for T7 RNA polymerase.

EXAMPLE 3

Expression of Recombinant OspA

For protein production, the plasmids were transferred to the expression strain BL21(DE3)/pLysS, a host strain containing a chromosomal copy of the gene for T7 RNA polymerase under control of the inducible lacUV5 promoter and a pACYC184 based plasmid, pLysS, which specifies low levels of T7 lysozyme, a natural inhibitor of T7 RNA polymerase. For additional information, see Moffatt, B. A., and Studier, F. W., "T7 Lysozyme inhibits transrciption by T7 RNA polymerase," *Cell*, 49:221–227 (1987). In uninduced cells, lysozyme reduces the basal activity of the T7 RNA polymerase and increases the range of target genes that can be stably maintained in the expression host.

Cultures of BL21(DE3)/pLysS carrying different plasmids were grown to mid-log phase, and a portion from each was induced with IPTG. Upon induction, plasmid pET9-preOspA was found to produce relatively small amounts of inducible protein which from analysis of SDS-polyacrylamide gels was very similar in mobility to wild-type OspA protein present in total extracts of *B. burgdorferi*. Referring to FIG. 10, samples (1.5μl) were removed for analysis by SDS-12.5% PAGE at the times indicated below. Proteins were visualized by staining with Coomassie blue. Lanes 1, 5 and 9 correspond to whole *B. burgdorferi* cells (5×10$^7$ cells) while lanes 2, 3 and 4 correspond to pET9-preOspA induced for 1, 3 or 18 hours. Lanes 6, 7 and 8 correspond to pET9-OspA induced for 1, 3 or 18 hours. The position of molecular weight markers (94, 67, 43, 30 and 20) are shown. Molecular masses of proteins are in kilodaltons.

Pulse-chase experiments were performed to demonstrate that synthesis of the preOspA protein ceased one to two hours after induction, a result which suggests that the protein is toxic to *E. coli*. In contrast, a much higher and sustained rate of expression was observed when pET9-OspA was induced.

FIG. 11 shows the induction of the recombinant variation of OspA followed by SDS-PAGE. Lane 1 was loaded with whole cells of uninduced BL21(DE3)/pLysS, pET9-OspA. Lanes 2–7 were loaded with whole cells sampled at one hour intervals after induction. Lane 8 contained molecular weight markers. FIG. 12 shows SDS-PAGE of the recombinant version of OspA at different stages of purification as follows: Lane 1, molecular weight markers; Lane 2, crude extract prior to centrifugation; Lane 3, crude extract after centrifugation; Lane 4, Q Sepharose flow through; Lane 5, S Sepharose gradient fraction; and Lane 6, hydroxylapatite fraction. Lanes 2–6 each contain 0.01% of the total protein present in each fraction. Proteins were analyzed on a 10–20% acrylamide gradient gel. Western blot analysis with two monoclonal antibodies, H5332 and H3TS, known to recognize different epitopes within wild-type OspA, was also performed to verify that these bands contained authentic OspA sequences. See Brandt, M. E., Riley, B. S., Radolf, J. D., and Norgard, M. V., "Immunogenic integral membrane proteins of *B. burgdorferi* are lipoproteins," *Infect Immun.*, 58:983–991 (1990). See also Howe, T. R., Mayer, L. W., and Barbour, A. G., "A single recombinant plasmid expressing two major outer surface proteins of the Lyme disease spirochete," *Science* 227:645–646 (1985).

Figure 13:
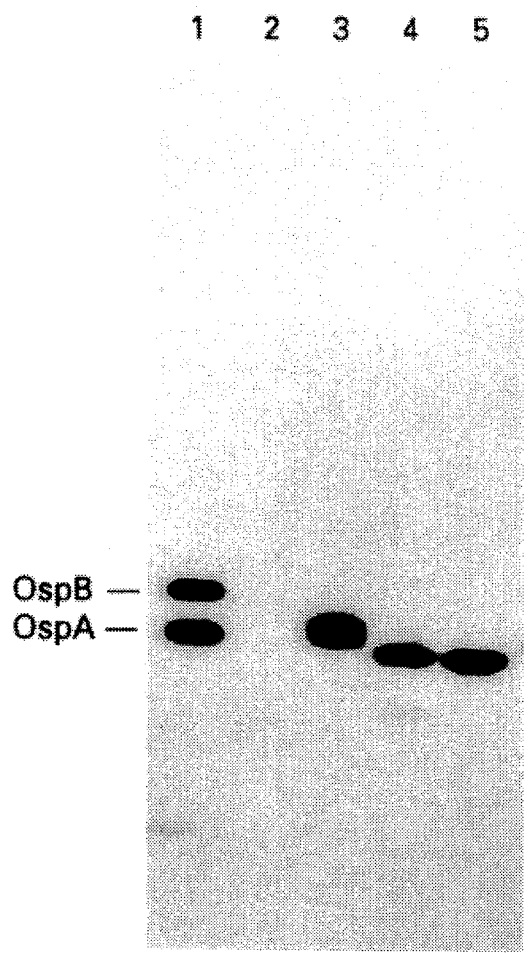
FIG. 13 is an autoradiogram of a Western blot immunochemical analysis of OspA and OspB proteins from whole *B. burgdorferi* cells as well as OspA and preOspA.

Referring again to FIG. 10, the protein corresponding to pET9-OspA was noticeably smaller than that produced by pET9-preOspA, even though both proteins were expected to contain approximately the same number of amino acid residues after processing to remove either the 17 residue long sequence in the case of wild-type OspA or just the initiating methionine from the recombinant variation of OspA. The most likely explanation for the difference was that the presence of covalently attached N-terminal lipid decreased the mobility of the processed pET9-preOspA product. On some gels (see FIG. 13 for example) the preOspA product migrated as two closely spaced bands, which may have represented processing intermediates.

EXAMPLE 4

Cellular localization of Recombinant Wild-type OspA and Soluble Variant OspA In order to determine subcellular localization, a 20 ml culture of BL21(DE3)/pLysS, PET9-preOspA was harvested by centrifugation at 8,000 rpm 3 ½ hours after IPTG induction. The resulting pellet was suspended in a 10 ml mixture containing 20 mM Tris-HCl (pH 8.0), 20 mM NaCl and 2 mM EDTA. The cells were subsequently lysed by freezing and thawing. The lysate was treated with Dnase and Mg$^{++}$, then centrifuged for 90 minutes at 33,000 rpm. The pellet fraction was resuspended in a 5 ml mixture containing 0.25 M sucrose, 3.3 mM Tris-HCl (PH 8.0), 1 mM DTT and 1mM EDTA. The resuspension was re-pelleted by centrifugation for 1 hour at 50,000 rpm. The pellet was resuspended in 1 ml 25% (w/w) sucrose, 5 mM EDTA and 1 mM DTT and subsequently layered onto a discontinuous sucrose gradient. Centrifugation was performed at 30,000 rpm for 16 hours at 4° C. After centrifugation, 0.5 ml fractions were collected and 20μl samples were analyzed by SDS-PAGE and Western blotting. The outer membrane region of the gradient was determined by its reactivity with antibody to OmpA, a well-characterized *E. coli* outer membrane component. See Zimmerman, R., and Wickner, W., "Energetics and intermediates of the assembly of protein OmpA into the outer membrane of *Escherichia coli*," *J. Biol. Chem.*, 258:3920–3925 (1983).

Almost all the full-length, wild-type OspA resulting from pET9-preOspA was recovered in the low-speed pellet fraction of the freeze-thaw cell lysate. The pellet was fractionated into inner and outer membranes by centrifugation through discontinuous sucrose gradients. Most of the protein was found in fractions enriched in inner membrane components.

Further studies demonstrated that this recombinantly-derived, wild-type version of OspA (preOspA) could only be extracted under conditions known in the art to selectively solubilize *E. coli's* inner membrane. Such conditions required the treatment of the protein fraction with a detergent such as Triton X-100 or sodium N-lauryl sarcosinate. For example, see Forst, S., Delgado, J., Ramakrishnan, G., and Inouye, M., "Regulation of ompC and ompF expression in *Escherichia coli* in the absence of envZ," *J. Bacteriol.*, 170:5080–5085 (1988). In contrast, the product of pET9-

OspA is soluble in the absence of any detergent at concentrations of ≧50 mg/ml. In addition, significant amounts of this recombinant variation of OspA (≧50% of the total cellular protein) can be produced from this plasmid several hours after induction with IPTG (see FIG. 11). When induction of pET9-OspA was continued longer than 6 hours, the cells began to lyse and eventually all the product was found in the culture supernatant.

EXAMPLE 5

Purification of Recombinant Soluble Variant OspA

In order to purify the recombinant variation of OspA, a three step procedure was employed. A 500 ml culture of *E. coli* BL21(DE3)/pLysS containing pET9-OspA was grown in shaking 2-liter flasks at 37° C. in tryptone broth supplemented with M9 salts, 0.4% glucose, 25 µg/ml chloramphenicol and 25 µg/ml kanamycin sulfate until the $OD_{600}$ reached 0.6, at which point IPTG was added to a final concentration of 0.5 mM. An additional 100 µg/ml kanamycin was added along with the IPTG to prevent overgrowth of the culture by any cells that might have lost the target plasmid. Six hours later, the cells were collected by centrifugation and resuspended in 25–30 ml of 20 mM sodium phosphate buffer (pH 7.7) and stored at −20° C. The crude extract was prepared by thawing the resuspended cells at 4° C., which allows the lysozyme encoded by pLysS to efficiently lyse the cells. This was followed by the addition of $MgCl_2$ and DNase (final concentrations of 2.5 mM and 5µg/ml, respectively). After 30 minutes at 4° C., cell debris was removed by centrifugation (15 minutes, 15,000g). The resulting pellet was extracted with 10 ml of 10 mM sodium phosphate buffer (pH 7.7) containing 10 mM NaCl (buffer A). After recentrifugation, the supernatants were combined to yield approximately 40 ml of crude extract.

The crude extract was applied at room temperature to a prepacked 25-ml bed of Q Sepharose fast flow which had been equilibrated with buffer A. The column was eluted with 50 ml of buffer A. Essentially all of the target protein was recovered in the flow through buffer.

The fractions containing target protein were dialyzed overnight at 4° C. versus 2×2-liter changes of 10 mM sodium phosphate buffer (pH 6.0) containing 5 mM NaCl (buffer B), clarified by centrifugation at 10,000g, and then applied at room temperature to a 20×1.5 cm column of S Sepharose Fast Flow equilibrated with buffer B. After washing the column with 100 ml of buffer B to remove unbound proteins and contaminants that absorb strongly at 260 nm, the bound target protein was eluted with a linear 300 ml gradient of 0–100 mM NaCl in buffer B, the elution of the target protein occurring at about 35 mM NaCl. Q Sepharose Fast Flow and S Sepharose Fast Flow were obtained from Pharmacia, Piscataway, N.J.

The pooled fractions of the target protein resulting from the S Sepharose step were loaded onto a 20 ml bed of Bio-Gel HTP hydroxyapatite previously equilibrated with buffer B. The column was run at room temperature and washed with 50 ml of buffer B. The protein was eluted with a linear 300-ml gradient of 100–400 mM sodium phosphate (pH 6.0). Fractions containing the target protein, which elutes as a broad peak between 150–300 mM sodium phosphate, were pooled and concentrated in an ultrafiltration cell to a final volume of 5 ml. The concentrated protein solution was dialyzed against 10 mM sodium phosphate (pH 6.0), 50 mM NaCl (buffer D) and stored at 4° C. Bio-Gel HTP hydroxyapatite was purchased from Bio-Rad Laboratories, Richmond, Calif.

The foregoing method for purification of the recombinant protein product is merely illustrative of a suitable approach for purifying the protein of the present invention. Other suitable techniques known in the art could alternatively be employed for purification. For example, the S Sepharose fraction can be concentrated and applied to a column of Sephacryl S-200 (obtained from Pharmacia, Piscataway, N.J.) or other suitable gel filtration matrices.

The resulting yield was 60–70 mg of the recombinant variation of OspA as produced from a 500 ml starting culture. Referring to FIG. 11, this overall yield is approximately 50% as judged from the SDS-PAGE of individual fractions, indicating a high level of expression of the truncated version of the ospA gene in *E. coli*.

In another embodiment of the present invention, purification of the variant proteins can be further augmented by cloning into pET vectors which place a target coding sequence in frame with an N-terminal or C-terminal poly-$(His)_6$ tail (These vectors are available from Novagen, Inc., Madison, Wis.). The fusion tails can then be used for recovery and purification of the recombinant protein by immobilized metal chelate affinity chromatography (Cochrane, A. W. et al., *Virology* 173: 335 (1989); Kagedal, L. in *Protein Purification. Principles, high resolution methods and applications* p. 60, J-C Janson and L. Ruden, eds. (1989)). During chromatography the poly$(His)_6$ tail on the fusion protein shares a bound $Ni^{2+}$ or $Zn^{2+}$ ion with iminodiacetic acid groups covalently attached to a chromatographic support. This technique can be used under gentle conditions if the protein is soluble, as is the case with the recombinant variant lipoproteins. Bound material is eluted by washing with low pH buffer (pH 3 to 4) or by including a chelating agent such as EDTA in the eluent.

EXAMPLE 6

Characterization of Proteins

Protein samples of the recombinant variation of OspA were analyzed by polyacrylamide gel electrophoresis under denaturing conditions. For technique, see Studier, F. W., "Analysis of bacteriophage T7 early RNAs and proteins on slab gels," *J. Mol. Bio.*, 79:237–248 (1973). Gels were fixed and stained with Coomassie blue and the separated proteins were electrophoretically transferred to nitrocellulose membranes, exposed to antibody directed against OspA and probed with [$^{125}$I]-labeled protein A to detect bound immunoglobulin See Barbour, A. G., "Biology of the Borrelia species," *Yale J Biol Med.*, 57:581–586 (1984). [$^{125}$I]-labeled protein A (5×10$^5$ cpm/ml) was obtained from DuPont-New England Nuclear.

In some cases, the nitrocellulose membranes were blocked with 3% gelatin in 20 mM Tris-HCl (pH 7.5), 500 mM NaCl (TBS) for a minimum of 1 hour and then washed with TBS containing 0.05% Tween 20 (TTBS) before reaction with antibody. After removal of unbound antibody by several washes in TTBS, reactive proteins were detected by using affinity purified alkaline phosphatase conjugated goat anti-mouse antibody and alkaline phosphatase color development reagents.

The native molecular weight of OspA was determined by chromatography of the purified protein in buffer A containing 200 mM NaCl at a flow rate of 1.5 ml/min on a calibrated 2.5×120 cm Sephacryl S-200 column at 4° C. Twenty amino acid residues corresponding to the N-terminal nucleotide sequence were determined using the Edman degradation procedure on a Applied Biosystems 470A Microsequencer. Amino terminal sequencing of the first 20 residues of the recombinant variation of OspA gave a sequence identical with that predicted from the DNA sequence after processing to remove the first methionine residue. The molar extinction coefficient of the protein was calculated from knowledge of its amino acid composition from the equation $E_{M,\ nat} = (Abs_{nat})\ (E_{M,Gdn.HCl})/AbS_{Gdn.HCl}$. See Gill, S. C., and von Hippel, P. H., "Calculation of protein extinction coefficients from amino acid sequence data," *Anal. Biochem* 182:319–326 (1989). The resulting molar extinction coefficient ($E_{280}$) was $10.59 \times 10^3 M^{-1}$. This value was found to be in excellent agreement (±5%) with that obtained from analysis of the amino-acid composition of acid hydrolysates, derived from the recombinant variation of OspA, as well as being consistent with the figures regarding the resulting protein yield.

EXAMPLE 7

Reactivity of Recombinant Variant OspA with Human Antibodies Directed Against Wild-type *B. burgdorferi* OspA.

The reactivity of the recombinant variation of OspA was tested against human antibodies to the wild-type OspA. Sera from patients with Lyme disease contains antibodies to several *B. burgdorferi* outer membrane proteins, including OspA. Reactive synovial fluid from patients with chronic Lyme disease-related arthritis and OspA-specific antibody H3TS have been previously described. See Barbour, A. G., Burgdorfer, W., Grunwaldt, E., and Steere, A. C., "Antibodies of patients with Lyme disease to components of the Ixodes dammini spirochete," *J. Clin.* Invest., 72:504–515 (1983). See also Barbour, A. G., Heiland, R. A., and Howe, T. R., "Heterogeneity of major proteins in Lyme disease borrelia: a molecular analysis of North American and European isolates," *J Infect Dis.,* 52:478–484 (1985).

Referring to FIG. 13, antibodies present in synovial fluid from a patient with Lyme disease-related arthritis reacted strongly in Western blots with the 31-kDa and 34-kDa wild-type OspA and OspB proteins from *B. burgdorferi*. In addition, both forms of OspA synthesized in *E. coli* (the recombinant variation of OspA as well as the full-length, wild-type version of OspA synthesized as a control) also reacted strongly.

Referring again to FIG. 13, Lane 1 contained whole cell lysates ($2\times10^6$ cells) of *B. burgdorferi* (B31) spirochetes while Lanes 2–4 contained induced *E. coli* cells. Lane 5 contained the purified recombinant variation of OspA (0.5μg). Samples applied to Lanes 2–5 were derived from cells (6μL) carrying the pET9 vector plasmid, pET9-preOspA or pET9-OspA, respectively, 3 hours after induction. SDS-12.5% PAGE separated proteins were transferred to nitrocellulose, blocked overnight in 2% bovine serum albumin and then reacted with synovial fluid from a patient with Lyme disease. The blots were washed, incubated with [$^{125}$I]-labeled protein A and then exposed to film for autoradiography. The positions of wild-type *B. burgdorferi* OspA and OspB are indicated.

While the results show that both plasmids express immunoreactive OspA protein, the protein expressed from pET9-preOspA seemed to react more strongly than an equivalent amount of protein produced from pET9-OspA. Similar results were obtained when Immobilon™, a hydrophobic polyvinylidene difluoride based membrane, was used as the solid phase for protein blotting. It was postulated that this apparent difference in reactivity might have been caused by poorer transfer to or retention of the recombinant variation of OspA on the nitrocellulose membrane. The foregoing theory was subsequently tested by labeling induced cultures with [$^{35}$S]methionine (obtained from DuPont-New England Nuclear/specific activity =1165 Ci/mmol.). Autoradiography was used to follow the relative amounts of wild-type OspA as well as the recombinant variation of OspA present during each step of the Western blot analysis.

Cultures of BL21(DE3)/pLysS cells carrying pET9-preOspA or pET9-OspA were grown at 37° C. to mid-log phase in M9 medium and induced with IPTG. One hour later, each culture was labeled with 20μCi/ml [$^{35}$S]methionine for 5 minutes and 10μL portions were analyzed after electrophoresis 12.5% gels. Referring to FIGS. 14 through 18, Lane 1 in each panel contained whole, unlabeled, *B. burgdorferi* cells ($5\times10^7$ cells). Lanes 2 and 3 contained induced, labeled cells carrying pET9-preOspA or pET9-OspA, respectively. Proteins were visualized by staining with Coomassie blue as shown in FIG. 14 and by autoradiography of the gel as shown in FIG. 15. In FIGS. 16 and 17, the proteins are visualized after electrophoretic transfer to nitrocellulose paper. FIG. 16 shows an autoradiogram of the nitrocellulose before further Western analysis. FIG. 17 shows an autoradiogram after probing with antibodies. FIG. 18 shows a photograph of the completed Western blot after treatment with alkaline phosphatase color development reagents. The solid arrows point to the recombinant variation of OspA as well as pET9-preOspA proteins shown in Lanes 1 and 2, respectively. The dashed arrows indicate the position of the pET9-OspA protein product which appears in Lane 3.

Referring now to FIGS. 14 through 18, it is apparent that the relative amounts of the wild-type OspA and the recombinant variation of OspA changed during the blotting procedure. The amount of the recombinant variation of OspA which remained after the blot was probed with antibodies and subsequently washed, was considerably reduced relative to the amount initially transferred. In contrast, the wild-type version of OspA was well retained during each step. The results demonstrated that the apparent difference in reactivity of the two forms of OspA (the recombinant variation and the wild-type version) was primarily due to a selective loss of the highly soluble, recombinant variation of OspA during Western blot analysis.

Construction of Soluble Variants of *B. burgdorferi* OspB and *B. hermsii* Vmp7.

The production of truncated nucleotide sequences coding for soluble OspB and Vmp7 was accomplished using the same strategy and techniques as were used to make the soluble OspA variant. However, because the nucleotide sequences of the wild-type OspA and OspB and Vmp7 differ from each other, new oligonucleotide primers had to be designed as described below.

Total genomic DNA containing the full-length, wild-type *B. burgdorferi* (B31 strain) ospB gene was isolated and purified. A set of oligonucleotide primers (see SEQ ID NO: 14, FIG. 19*a* and SEQ ID NO: 16, FIG. 19*c*) was synthesized for use in the PCR allowing for the specific amplification of a truncated version of the ospB gene lacking the first 16 codons. Use of these primers also resulted in the inclusion of preferred restriction sites before and after the coding sequence of the amplified product. A second set of oligonucleotide primers (see SEQ ID NO: 15, FIG. 19b and SEQ ID NO: 16, FIG. 19c) was also synthesized for use in the PCR to allow for the specific amplification of the entire wild-type ospB gene for use as a control.

The method used to construct the Vmp7 variant was essentially the same as that used to construct the OspA and OspB variants. However, the starting material for the template DNA was B. hermsii DNA, and the oligonucleotide primers were those described by SEQ ID NO: 17, FIG. 20a and SEQ ID NO: 18, FIG. 20b. In the case of the Vmp7, no full-length control protein was made.

Figure 24A:
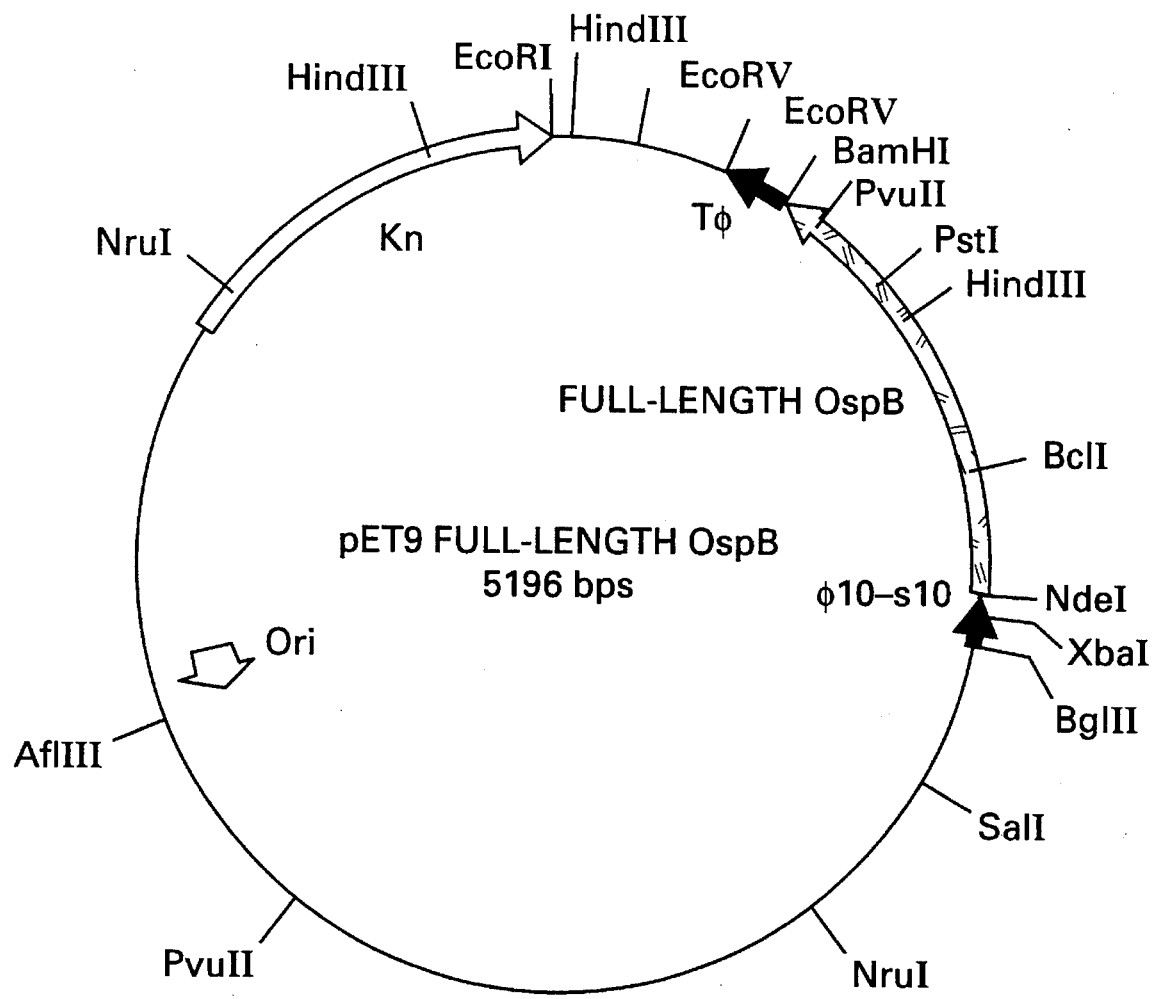
FIG. 24a is a schematic representation of plasmid pET9-preOspB.
Figure 24B:
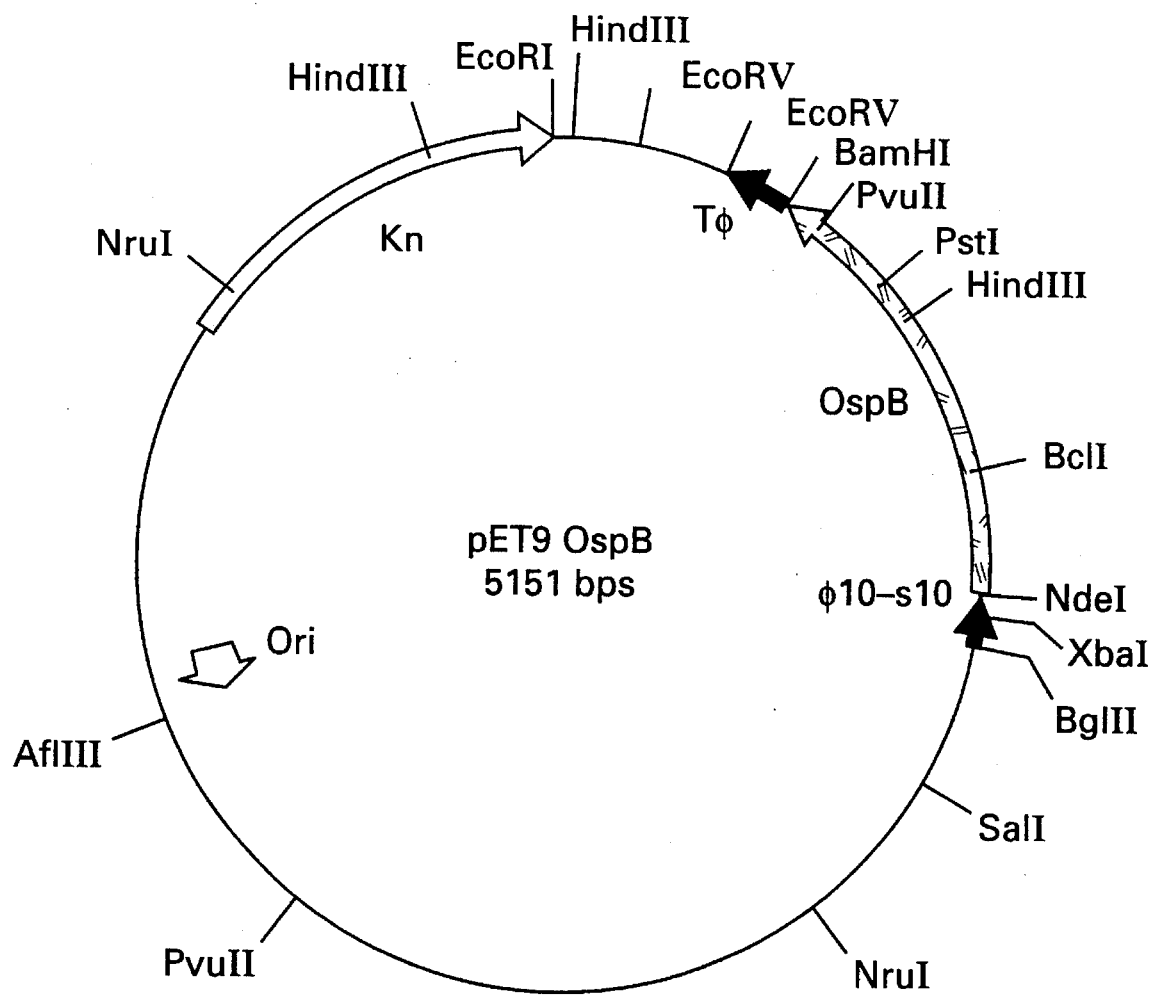
FIG. 24b is a schematic representation of plasmid pET9-OspB.
Figure 25:
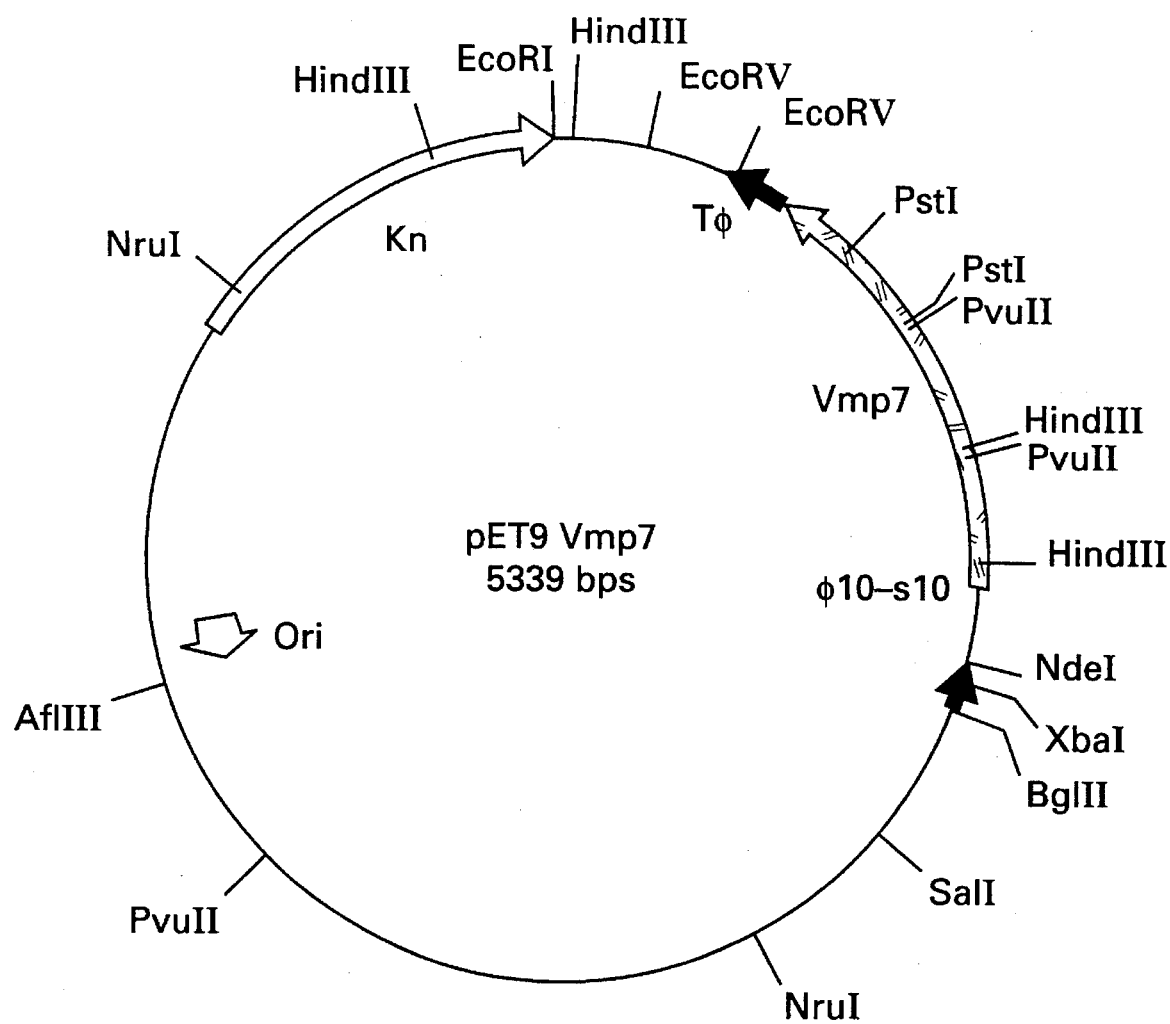
FIG. 25 is a schematic representation of plasmid pET9-Vmp7.

The DNA fragments produced by the PCR were purified and then subcloned into the pET9 expression vector using the same methods as were used to produce the ospA variant. The resulting plasmids were called pET9-preOspB (pET9 with full-length OspB inserted; FIG. 24a), pET9-OspB (pET9 with truncated OspB inserted; FIG. 24b) and pET9-Vmp7 (pET9 with truncated Vmp7 inserted; FIG. 25). These expression vectors were then transferred to a host expression strain for protein production. FIG. 28 depicts the nucleotide sequence and the amino acid sequence of the translation product of the soluble variant OspB gene, SEQ ID NO: 21. FIG. 29 depicts the nucleotide sequence and the amino acid sequence of the translation product of the soluble variant of the Vmp 7 gene, SEQ ID NO: 22.

The recombinant variants of OspB and Vmp7 of the present method have been characterized and found to behave like the OspA variant with respect to solubility in low ionic strength buffers in the absence of detergent, specific antigenic reactivity with antibodies to the wild-type protein, native (i.e., non-denatured) configuration upon purification, presence in cell extracts as a monomer as opposed to an aggregate, and the ability to be expressed at very high levels in the host cell.

EXAMPLE 8

Primers Used to construct Soluble Variants of OspB

The three primers used to construct the truncated variations of OspB (and the full-length OspB control) are depicted at FIGS. 19a, 19b and 19c. The underlined portions of the primers depicted in these Figures highlight the regions of the primers which have homology to wild-type B. burgdorferii DNA. The regions in bold type depict the restriction sites which have been included in the design of the primers in order to facilitate subcloning of the amplification products into an appropriate expression vector.

The synthetic oligonucleotide #1104 (SEQ ID NO: 14, FIG. 19a) was used to change the DNA sequence at the beginning of the coding sequence of OspB (the amino terminus of the protein). A PCR reaction including primers #1104 and #1106 (see below), and wild-type OspB as the DNA template, results in the DNA sequence for the full-length OspB (preOspB) protein containing the signal sequence for lipidation (See SEQ ID NO: 19 for the full-length OspB protein, and FIG. 21a for the signal sequence of lipidation). This primer contains a NdeI restriction site near its 5' end which enables the amplified OspB open-reading frame to be readily inserted in-frame into an appropriate vector such as pET9. The preOspB protein is expressed rather poorly in *Escherichia coli*.

The synthetic oligonucleotide #1105 (SEQ ID No: 15, FIG. 19b) was used to change the DNA sequence within the first part of the OspB coding sequence. The resulting sequence begins with a methionine codon placed just downstream of the cysteine codon which formed the amino terminal end of the processed wild-type lipoprotein. The primer contains a NdeI restriction site near its 5' end which enables the amplified ospB open-reading frame to be readily inserted in-frame into an appropriate vector such as pET9. When used in conjunction with Primer #1106 (see below) it eliminates the region of the wild-type gene coding for the lipidation signal sequence. The protein resulting from expression of this construct is not lipidated, is expressed at very high levels and can be purified easily to homogeneity. The DNA sequence encoding the amino terminus of the truncated OspB protein (SEQ ID NO: 21) is depicted at FIG. 21c. FIG. 21a depicts the 5' and 3' ends of the wild-type ospA gene, showing where the primers anneal.

The oligonucleotide #1106 (SEQ ID NO: 16, FIG. 19c) was used to change the sequence at the 3' end of the coding sequence for the OspB gene. This primer is used in conjunction with #1104 or #1105 to prime DNA synthesis from the carboxyl-terminus of the OspB coding sequence and it includes the translational stop codon to end the open reading frame. The primer contains a BamHI restriction site near its 5' end which enables the amplified OspB open-reading frame to be readily inserted into an appropriate vector such as pET9. Because it primes DNA synthesis of the second strand, it anneals to the DNA in the reverse polarity. As shown in FIG. 21a and b, the DNA product resulting from amplification from this primer differs from the wild-type only in non-coding sequences at the 3' end.

DNA Synthesis

FIGS. 21a, b and c depict portions of the template DNA and portions of the amplification products resulting from PCR using each set of primers described above. The underlined regions indicate portions of the OspB primers which are complementary to *Borrelia burgdorferi* OspB DNA. Regions in bold indicate portions providing unique restriction enzyme recognition sites that are added as part of the design of the PCR primers—CATATG is for the enzyme NdeI which is used to define the beginning of the coding sequence in subsequent clones in pET9 vectors, GGATCC is for the enzyme BamHI which delimits the end of the DNA inserted into the pET9 vector.

EXAMPLE 9

Primers Used to Construct Soluble Variants of Vmp7

The two primers used to construct the truncated variations of Vmp7 are depicted at FIGS. 20a and 20b. The underlined portions of the primers depicted in these Figures highlight the regions of the primers which have homology to wild-type *B. hermsii* DNA. The regions in bold type depict the restriction sites which have been included in the design of the primers in order to facilitate subcloning of the amplification products into an appropriate expression vector.

Like the coding sequence for the related wild-type *B. burgdorferi* outer surface lipoproteins, the coding sequence for wild-type Vmp7 (SEQ ID NO: 20) encodes a signal peptidase II signal sequence at its 5' end (See FIG. 22a). The synthetic oligonucleotide Vmp7-2 (SEQ ID NO: 17, FIG. 20a) was used to change the DNA sequence within the first part of the Vmp7 coding sequence (the amino terminus of the protein) in order to eliminate the region coding for the signal sequence. The primer contains a NdeI restriction site near the 5' end which enables the amplified Vmp7 open-reading frame to be readily inserted into an appropriate vector such as pET9. In addition, the primer was designed to insert an extra amino acid residue (alanine) just after the initiating methionine to insure that the initiating methionine is efficiently removed in vivo (See FIG. 22b). Addition of this alanine residue also makes all three truncated proteins described herein (OspA, OspB and Vmp7) start with the same dipeptide.

The oligonucleotide Vmp7-3 (SEQ ID NO: 18, FIG. 20b) was used to change the sequence at the 3' end of the coding sequence for the vmp7 gene. It is used in conjunction with Vmp7-2 to prime DNA synthesis from the carboxyl-terminus of the vmp7 coding sequence and it includes the translational stop codon to end the open reading frame. The primer contains a BglII restriction site near its 5' end which enables the amplified vmp7 open-reading frame to be readily inserted into an appropriate vector such as pET9. Because it primes DNA synthesis of the second strand, it anneals to the DNA in the reverse polarity (See FIG. 22b).

The resulting protein is not lipidated, is expressed at very high levels and can be purified easily to homogeneity. The DNA encoding this protein is described at SEQ ID NO: 22. The 5' and 3' ends of the DNA encoding the recombinant variant are depicted at FIG. 22b.

DNA Synthesis

FIGS. 22a and 22b depict portions of the template DNA and portions of the amplification products resulting from PCR using the set of primers described above. The underlined regions indicate portions of the Vmp7 primers which are complementary to Borrelia hermsii DNA. Regions in bold indicate portions providing unique restriction enzyme recognition sites that are added as part of the design of the PCR primers—CATATG is for the enzyme NdeI which is used to define the beginning of the coding sequence in the subsequent clone in a pET9 vector; AGATCT is for the enzyme BglII which delimits the end of the DNA inserted into the pET9 vector.

EXAMPLE 10

High level Expression of Recombinant Truncated OspA, OspB and Vmp7

Figure 23:
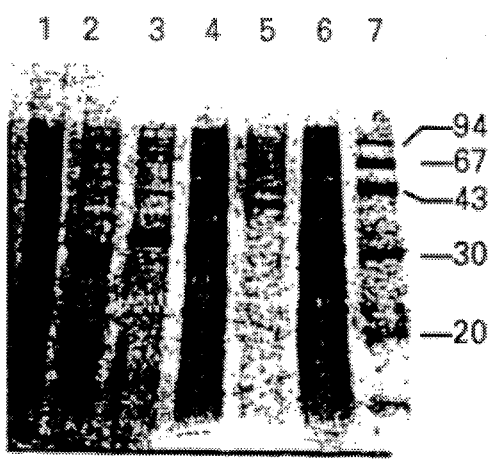
FIG. 23 is a photograph of a SDS-12% PAGE gel stained with Coomassie blue upon which various cellular protein samples were run subsequent to IPTG induction.

FIG. 23 represents PAGE electrophoresis of whole cell extracts of cells harboring each of the expression plasmids, pET9-OspA, pET-OspB and pET-Vmp7. The major band in each sample lane is the truncated variation of the wild-type lipoprotein, clearly demonstrating that these proteins are expressed at high levels in a bacterial host.

Cultures of BL21(DE3)/pLysS, each carrying either pET9-OspA, pET-OspB or pET-Vmp7, were grown to mid-log phase and then induced by addition of IPTG (final concentration 0.5 mM). Four hours after induction a portion of each culture (5 microliters) was removed for analysis by SDS-12% PAGE. Proteins were visualized by staining with Coomassie blue. Lanes 1, 4 and 6 were loaded with 5×10$^7$ B. burgdorferi cells. Lane 2 represents whole cell extracts from induced cultures harboring pET9-OspA; lane 3 represents whole cell extracts from induced cultures harboring pET9-OspB; lane 5 represents whole cell extracts from induced cultures harboring pET9-Vmp7; and lane 7 shows molecular weight markers. The molecular masses of the markers are shown in kilodaltons.

Conclusions and Summary of Data

While the foregoing method of producing a recombinant version of a protein was directed to outer surface proteins A and B of Borrelia burgdorferi, and variable major protein 7 of Borrelia hermsii, the method is equally applicable to other Borrelia lipoproteins, provided that the signal sequence for signal peptidase II appears in the gene coding for the lipoprotein in question.

The truncated versions of the lipoprotein genes were excellent overproducers due to their lack of association with the host cell membrane. The resulting recombinant variations of OspA, OspB and Vmp7 each accounted for more than 50% of the total cellular protein after a few hours of induction. See examples 4, 5 and 6, and FIG. 23.

In addition, the recombinant variants of these lipoproteins are not lipidated and are highly soluble ($\geq 50$ mg/ml) in the absence of detergents. See example 4. Moreover, 60–70 mg of pure protein is available from as little as 0.5 liters of starting culture after a simple purification procedure. See examples 5 and 6. Western blots of the recombinant variation of OspA demonstrated that the truncated recombinant OspA retained immunoreactive epitopic sites. See examples 3 and 7. This specific immunoreactivity, in conjunction with the high level of expression and solubility in the absence of detergents, make the proteins of the present invention good candidates for diagnostic agents to detect the presence of Lyme disease and relapsing fever in clinical isolates. These same characteristics also recommend these truncated lipoproteins for potential vaccine immunogens against Borrelia pathogens.

Equivalents

Those skilled in the art will recognize, or be able to ascertain using no more than routine experimentation, many equivalents to the specific embodiments described herein. Such equivalents are intended to be encompassed by the following claims.

---

We claim:

1. A recombinant soluble variant of a Borrelia outer surface lipoprotein wherein the amino acid sequence is SEQ ID NO: 4, except that the penultimate amino terminal amino acid residue is replaced with one selected from the group consisting of: glycine, proline, serine, threonine and valine.

2. A recombinant variant of a Borrelia outer surface lipoprotein wherein the variant is isolatable, without use of detergent, from cytosol of cells bearing a variant-encoding gene, and wherein the amino acid sequence is SEQ ID NO: 23, except that the penultimate amino terminal amino acid residue is replaced with one selected from the group consisting of: glycine, proline, serine, threonine and valine.

3. A recombinant variant of a Borrelia outer surface lipoprotein wherein the variant is isolatable, without use of detergent, from cytosol of cells bearing a variant-encoding gene, and wherein the amino acid sequence is SEQ ID NO: 24, except that the penultimate amino terminal amino acid residue is replaced with one selected from the group consisting of: glycine, proline, serine, threonine and valine.

4. DNA having a nucleotide sequence selected from the group consisting of: SEQ ID NO: 3, SEQ ID NO: 21 and SEQ ID NO: 22.

5. A nucleic acid having a nucleotide sequence which encodes an amino acid sequence selected from the group consisting of: SEQ ID NO: 4, SEQ ID NO: 23 and SEQ ID NO: 24.

6. A protein having an amino acid sequence selected from the group consisting of: SEQ ID NO: 4, SEQ ID NO: 23 and SEQ ID NO: 24.

7. A DNA vector comprising a DNA sequence which encodes an amino acid sequence selected from the group consisting of: SEQ ID NO: 4, SEQ ID NO: 23 and SEQ ID NO: 24.

8. A host cell which produces a protein having an amino acid sequence selected from the group consisting of: SEQ ID NO: 4, SEQ ID NO: 23 and SEQ ID NO: 24.

* * * * *